(12) United States Patent
Ortiz et al.

(10) Patent No.: US 12,371,427 B2
(45) Date of Patent: Jul. 29, 2025

(54) POLYMORPHIC FORMS OF A SUBSTITUTED-QUINOXALINE-TYPE BRIDGED-PIPERIDINE COMPOUND

(71) Applicant: Purdue Pharma L.P., Stamford, CT (US)

(72) Inventors: Ronnie Ortiz, Wake Forest, NC (US); David Igo, Raleigh, NC (US); Naoki Tsuno, Toyonaka (JP); Mayu Fukuda, Amagasaki (JP); Naoki Miyake, Amagasaki (JP)

(73) Assignee: Purdue Pharma L.P., Stamford, CT (US)

( * ) Notice: Subject to any disclaimer, the term of this patent is extended or adjusted under 35 U.S.C. 154(b) by 1013 days.

(21) Appl. No.: 17/310,380

(22) PCT Filed: Jan. 30, 2020

(86) PCT No.: PCT/IB2020/050741
§ 371 (c)(1),
(2) Date: Jul. 29, 2021

(87) PCT Pub. No.: WO2020/157691
PCT Pub. Date: Aug. 6, 2020

(65) Prior Publication Data
US 2022/0098186 A1   Mar. 31, 2022

Related U.S. Application Data

(60) Provisional application No. 62/799,710, filed on Jan. 31, 2019.

(51) Int. Cl.
*C07D 453/02* (2006.01)
*C07C 309/30* (2006.01)

(52) U.S. Cl.
CPC .......... *C07D 453/02* (2013.01); *C07C 309/30* (2013.01); *C07B 2200/13* (2013.01)

(58) Field of Classification Search
CPC .. C07D 453/02; C07C 309/30; C07B 2200/13
See application file for complete search history.

(56) References Cited

U.S. PATENT DOCUMENTS

| | | | |
|---|---|---|---|
| 5,698,155 | A | 12/1997 | Grosswald et al. |
| 6,572,891 | B1 | 6/2003 | Ugarkovic |
| 7,749,533 | B2 | 7/2010 | Fu et al. |
| 8,476,271 | B2 | 7/2013 | Tsuno et al. |
| 8,846,929 | B2 | 9/2014 | Fuchino et al. |
| 9,145,408 | B2 | 9/2015 | Tsuno et al. |
| 9,241,910 | B2 | 1/2016 | Kurasawa et al. |
| 9,278,967 | B2 | 3/2016 | Fuchino et al. |
| 9,308,175 | B2 | 4/2016 | Pellikaan et al. |
| 9,527,840 | B2 | 12/2016 | Fuchino et al. |
| 2016/0009717 | A1 | 1/2016 | Fuchino et al. |

FOREIGN PATENT DOCUMENTS

| | | | |
|---|---|---|---|
| WO | 2009/027820 A2 | 3/2009 | |
| WO | WO-2010010458 A1 * | 1/2010 | ................ A61P 1/10 |
| WO | 2014/020405 A1 | 2/2014 | |
| WO | 2014/102592 A2 | 7/2014 | |
| WO | WO-2018020418 A1 * | 2/2018 | ........... A61K 31/498 |

OTHER PUBLICATIONS

International Search Report corresponding to International Patent Application No. PCT/IB2020/050741 dated Mar. 16, 2020.
International Written Opinion corresponding to International Patent Application No. PCT/IB2020/050741 dated Mar. 16, 2020.
"Handbook of Organic Compound Crystal Production—Principles and Know-How," pp. 57-79 (Jul. 2008).
Kawaguchi, Y., et al., "Drug and Crystal Polymorphism" Journal of Human Environmental Engineering 4(2):310-317, Architectural Institute of Japan, Japan (2002).
Pharmaceutical Affairs Bureau, "Test Procedures and Acceptance Criteria for New Drug Substances and New Drug Products," Notification #568 (May 2001).
Takada, N., "API form screening and selection in drug discovery stage," Pharm Stage 6(10):20-25, J-Stage, Japan (Jan. 2007).
Yamano, M., "Approach to Crystal Polymorph in Process Research of New Drug," Journal of Synthetic Organic Chemistry 65(9):907-913, J-Stage, Japan (2007).
English Translation of Office Action for Japanese Patent Application No. 2021-544362, dated Aug. 29, 2023.

(Continued)

*Primary Examiner* — Joseph K McKane
*Assistant Examiner* — Jalisa Holmes Ferguson
(74) *Attorney, Agent, or Firm* — Sterne, Kessler, Goldstein & Fox

(57) ABSTRACT

Provided herein are novel crystalline forms of a crystalline compound of Formula (I), which modulates the ORL-1 receptor. The crystalline compounds of Formula (I), compositions thereof, and methods of using thereof that are described herein are particularly useful for treatment, prevention, and management of several sleep disorders.

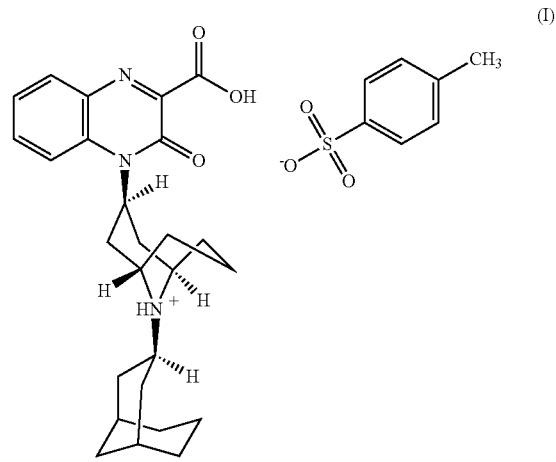

20 Claims, 9 Drawing Sheets

(56) References Cited

OTHER PUBLICATIONS

Figure 1:
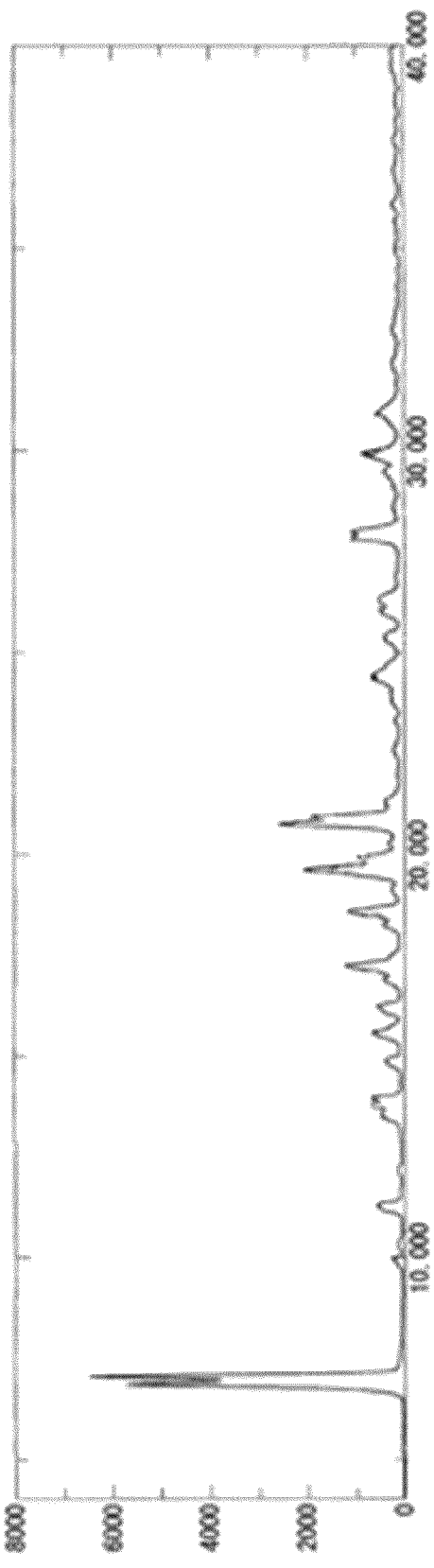

Gu, H., et al., "Grouping Solvents by Statistical Analysis of Solvent Property Parameters: Implication to Polymorph Screening," Int. J. Pharm., 283:117-125, Elsevier, Netherlands (Jun. 2004).

Gu, H., et al., "Polymorph Screening: Influence of Solvents on the Rate of Solvent-Mediated Polymorphic Transformation," J. Pharm. Sci., 90:1878-1890, Elsevier, Netherlands (Jun. 2001).

Singhal, D., et al., "Drug polymorphism and dosage form design: a practical perspective," *Advanced Drug Delivery Reviews* 56:335-347, Elsevier, Netherlands (2004).

Balbach, S., et al., "Pharmaceutical evaluation of early development candidates 'the 100mg-approach'", *International Journal of Pharmaceutics* 275:1-12, Elsevier, Netherlands (2003).

Caira, M.R., "Crystalline Polymorphism of Organic Compounds," in *Design of Organic Solids*, Weber, E., ed., pp. 163-204, Springer Verlag Berlin Heidelberg, Germany (1998).

Lee, E., "A practical guide to pharmaceutical polymorph screening & selection," Asian J Pharm Sci 9:163-175 (May 2014).

Hilfiker, R., ed., *Polymorphism: in the Pharmaceutical Industry*, Wiley-VCH Verlag GmbH & Co. KGaA, Weinheim, Germany (2006).

Hosseini, M.W., ed., *Molecular Networks*, Structure and Bonding, vol. 132, Mingos, D.M.P., series ed., Springer Berlin, Heidelberg, Germany (2009).

Bell, G., et al., "Water Activity Fails to Predict Critical Hydration Level for Enzyme Activity in Polar Organic Solvents: Interconversion of Water Concentrations and Activities," Enzyme and Microbial Technology 20(6):471-477, Elsevier, Netherlands (May 1997).

King, R.E., "Tablets, Capsules, and Pills," in *Remington's Pharmaceutical Sciences*, 16th Edition, Osol, A., ed., Chapter 89, pp. 1553-1593, Mack Publishing Co., Easton, United States (1980).

Padula, C., et al., "In Vitro Evaluation of Mucoadhesive Films for Gingival Administration of Lidocaine," AAPS PharmSciTech 14(4):1279-1283, American Association of Pharmaceutical Scientists, United States (Dec. 2013).

Pather, S.I., et al., "Current Status and the Future of Buccal Drug Delivery Systems," Expert Opinion on Drug Delivery 5(5):531-542, Informa Healthcare, United Kingdom (May 2008).

Radebough, G.W., et al., "Preformulation," in *Remington's Pharmaceutical Sciences*, vol. 2, 19th Edition, Gennaro, A.R., ed., Chapter 83, pp. 1447-1676, Mack Publishing, Easton, United States (1995).

Wilson, G.M., "Vapor-Liquid Equilibrium. XI. A New Expression for the Excess Free Energy of Mixing," Journal of the American Chemical Society 86(2):127-133, ACS Publications, United States (Jan. 1964).

* cited by examiner

POLYMORPHIC FORMS OF A SUBSTITUTED-QUINOXALINE-TYPE BRIDGED-PIPERIDINE COMPOUND

1. BACKGROUND

The ability to modulate the ORL-1 receptor presents an opportunity in drug discovery to administer this class of compounds for the treatment, prevention or management of certain disorders, such as pain. U.S. Pat. Nos. 8,476,271, 8,846,929, 9,145,408, 9,278,967, and 9,527,840 and U.S. Patent Application Publication No. US 2016/0009717 A1 each disclose substituted-quinoxaline-type bridged piperidine compounds that have affinity for the ORL-1 receptor.

Solid forms such as salts, crystal forms, e.g., polymorphic forms of a compound are known in the pharmaceutical art to affect, for example, the solubility, stability, flowability, fractability, and compressibility of the compound as well as the safety and efficacy of drug products based on the compound. So critical are the potential effects of solid forms in a single drug product on the safety and efficacy of the respective drug product that the United States Food and Drug Administration requires the identification and control of solid forms, e.g., crystalline forms of each compound used in each drug product marketed in the United States. Accordingly, new crystalline forms of drug compounds can further the development of drug formulations for the treatment, prevention or management of certain disorders, such as pain.

Citation of any reference in the Background section of this application is not to be construed as an admission that such reference is prior art to the present application.

2. SUMMARY

The invention provides crystalline forms of substituted-quinoxaline-type bridged piperidine compounds. One such compound has the following chemical structure described in Formula (I):

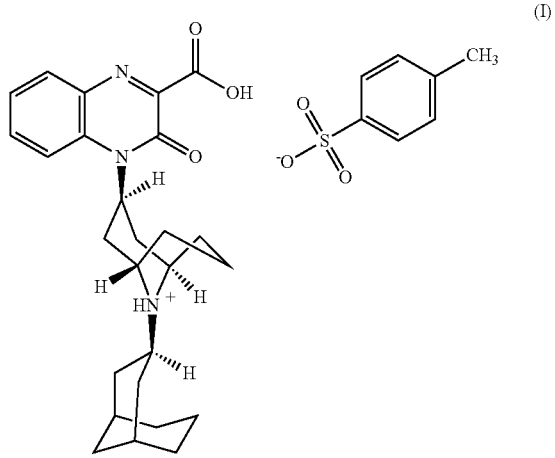

In particular, crystalline forms of a compound of Formula (I) are useful for the treatment, prevention or management of pain and sleep disorders. In addition, the present invention provides crystalline forms of a compound of Formula (I) with a crystalline purity of a single crystalline form that is greater than about 90%, relative to the total amount of all crystalline forms of the compound of Formula (I) present.

In certain embodiments, the invention provides bulk amounts of a crystalline or amorphous form of a compound of Formula (I). Such bulk amounts may include greater than about 1 kg, greater than about 10 kg, or greater than about 100 kg.

In certain embodiments, the crystalline forms of Formula (I) provided herein are characterized by powder X-ray diffraction ("PXRD" or "XRPD") crystallography. In one aspect of the invention, a non-solvated crystalline form of a compound of Formula (I), referred to herein as Form A, has a XRPD pattern that is substantially similar (e.g., 2Θ±0.2°) to that depicted in FIG. 3A. In another aspect of the invention, a crystalline form of a compound of Formula (I), referred to herein as Form B, has a XRPD pattern that is substantially similar (e.g., 2Θ±0.2°) to that depicted in FIG. 1. In another aspect of the invention, a hydrate crystalline form of a compound of Formula (I), referred to herein as Form C, has a XRPD pattern that is substantially similar (e.g., 2Θ±0.2°) to that depicted in FIG. 4A. In another aspect of the invention, a non-solvated crystalline form of a compound of Formula (I), referred to herein as Form D, has a XRPD pattern that is substantially similar (e.g., 2Θ±0.2°) to that depicted in FIG. 5A. In another aspect of the invention, a hydrate crystalline form of a compound of Formula (I), referred to herein as Form E, has a XRPD pattern that is substantially similar (e.g., 2Θ±0.2°) to that depicted in FIG. 7A.

Certain embodiments of the invention provide pharmaceutical compositions and dosage forms comprising a crystalline form of a compound of Formula (I) and a pharmaceutically-acceptable diluent, excipient or carrier. The invention further provides methods of their use for the treatment, prevention or management of sleep disorders. Such crystalline forms of a compound of Formula (I) exhibit affinity for the human ORL-1 receptor. In certain embodiments, the invention provides methods of making, isolating and/or characterizing a crystalline form of Formula (I), or an amorphous form of Formula (I). The crystalline forms of the invention are useful as active pharmaceutical ingredients for the preparation of formulations for use in animals or humans. Thus, the present invention encompasses the use of these crystalline forms in pharmaceutical compositions and dosage forms. The crystalline forms of Formula (I) in pharmaceutical compositions and dosage forms of the invention are useful, for example, for the treatment, prevention, or management of the diseases described herein. Pharmaceutical compositions and dosage forms can be formed with the crystalline forms of Formula (I) and one or more pharmaceutical carriers or excipients.

Compound forms and pharmaceutical compositions of the present invention are useful for treating or preventing a sleep disorder in a subject, e.g., a human. In one embodiment, an effective amount of a crystalline form of Formula (I) or pharmaceutical composition comprising the same, can be used to treat or prevent a sleep disorder including, but not limited to insomnia (e.g., "adult" insomnia, child insomnia, and middle-of-the-night insomnia); an alcohol-induced sleep disorder (e.g., insomnia-type alcohol-induced sleep disorder, daytime sleepiness-type alcohol-induced sleep disorder, parasomnia-type alcohol-induced sleep disorder, and mixed-type alcohol-induced sleep disorder); insomnia in alcohol use disorder; a sleep disturbance associated with alcohol cessation (e.g., insomnia associated with alcohol cessation); hypersomnia (such as insufficient sleep syndrome); circadian rhythm sleep-wake disorder (e.g., delayed sleep-wake phase, advanced sleep-wake phase, irregular sleep-wake rhythm, non-24-hour sleep-wake rhythm, shift work syndrome, and jet lag); or any combination thereof. When used to treat or prevent a sleep disorder, such as those included above, an effective amount of a crystalline form of Formula (I) or composition comprising the same, can be administered to a patient who is receiving one or more concomitant therapies for treating or preventing addictive alcohol use disorder.

In another embodiment, an effective amount of a crystalline form of Formula (I) or pharmaceutical composition comprising the same, can be used to treat or prevent a sleep disorder including, but not limited to an Insomnia Disorder (e.g., "adult" insomnia, child insomnia, and middle-of-the-night insomnia).

In another embodiment of the disclosure, an effective amount of a crystalline form of Formula (I) or pharmaceutical composition comprising the same, can be used to treat or prevent a sleep disorder including, but not limited to, an Insomnia Disorder associated with alcohol, e.g., insomnia-type alcohol-induced sleep disorder and mixed type alcohol-induced sleep disorder; insomnia in alcohol use disorder; insomnia associated with alcohol cessation; or any combination thereof.

It will be apparent to those skilled in the art that various modifications and variations can be made in the present invention without departing from the scope and spirit of the invention. Other embodiments of the invention will be apparent to those skilled in the art from consideration of the specification and practice of the invention disclosed herein. Applicants intend that the specification and examples be considered as exemplary, but not limiting in scope.

3. BRIEF DESCRIPTION OF THE FIGURES

FIG. 1 provides a XRPD pattern of Form B of Formula (I) prepared in Example 1 depicting intensity (counts)(y-axis) and 2-theta (° 2Θ)(x-axis).

Figure 2:
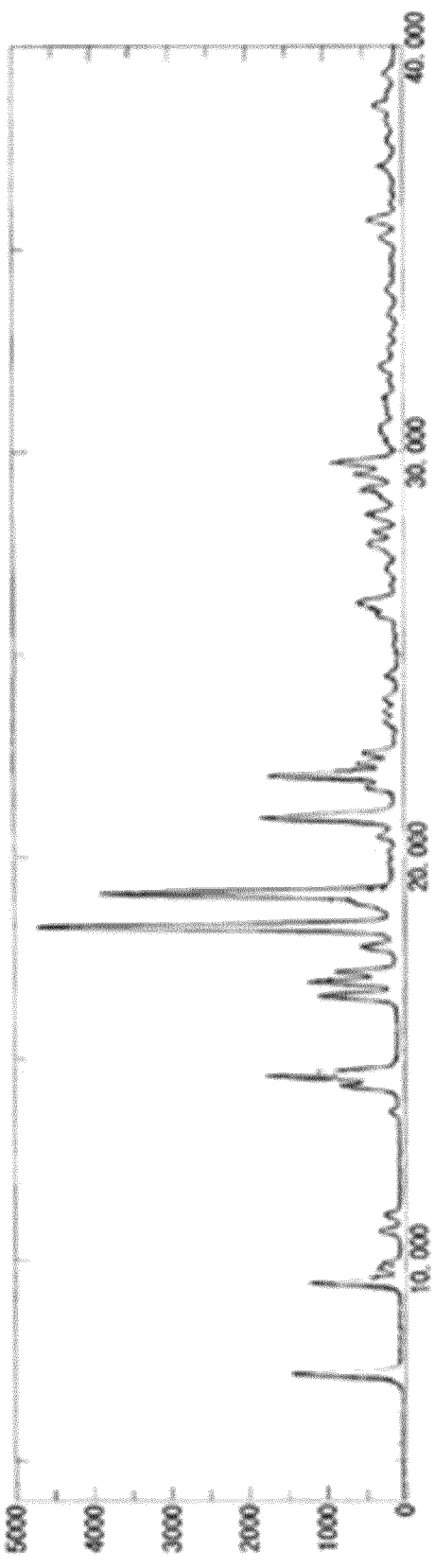

FIG. 2 provides a XRPD pattern of Form A of Formula (I) prepared in Example 1 depicting intensity (counts)(y-axis) and 2-theta (° 2Θ)(x-axis).

Figure 3A:
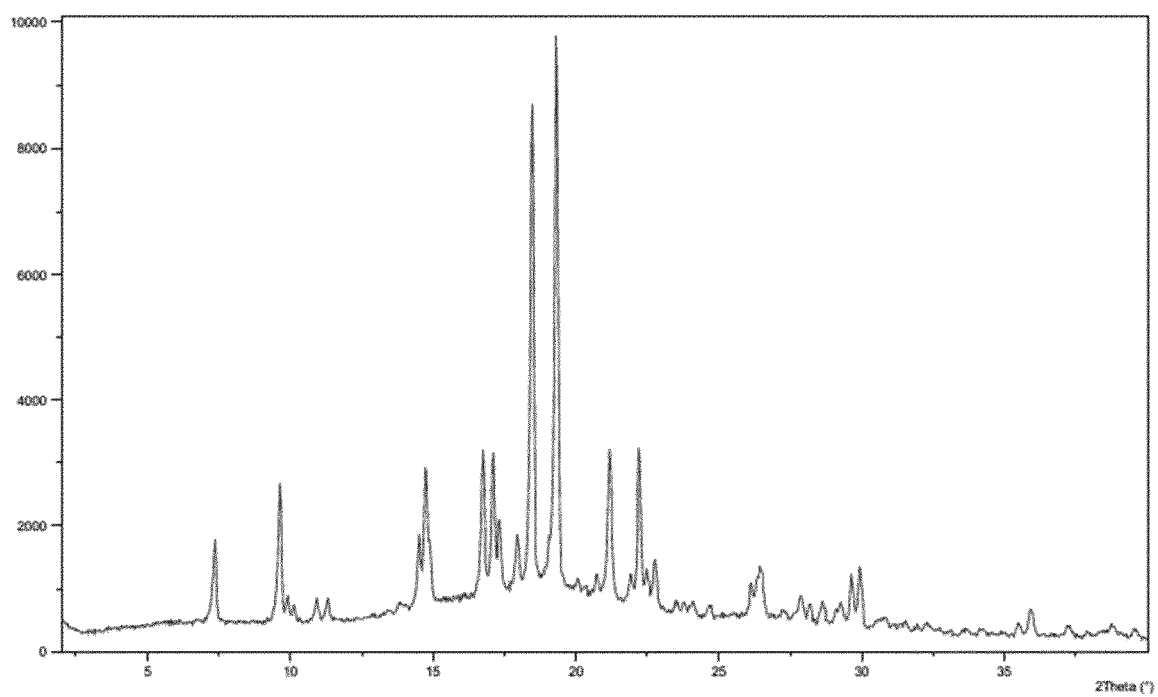

FIG. 3A provides a XRPD pattern of Form A of Formula (I) prepared in Example 3 depicting intensity (counts)(y-axis) and 2-theta (° 2Θ)(x-axis).

Figure 3B:
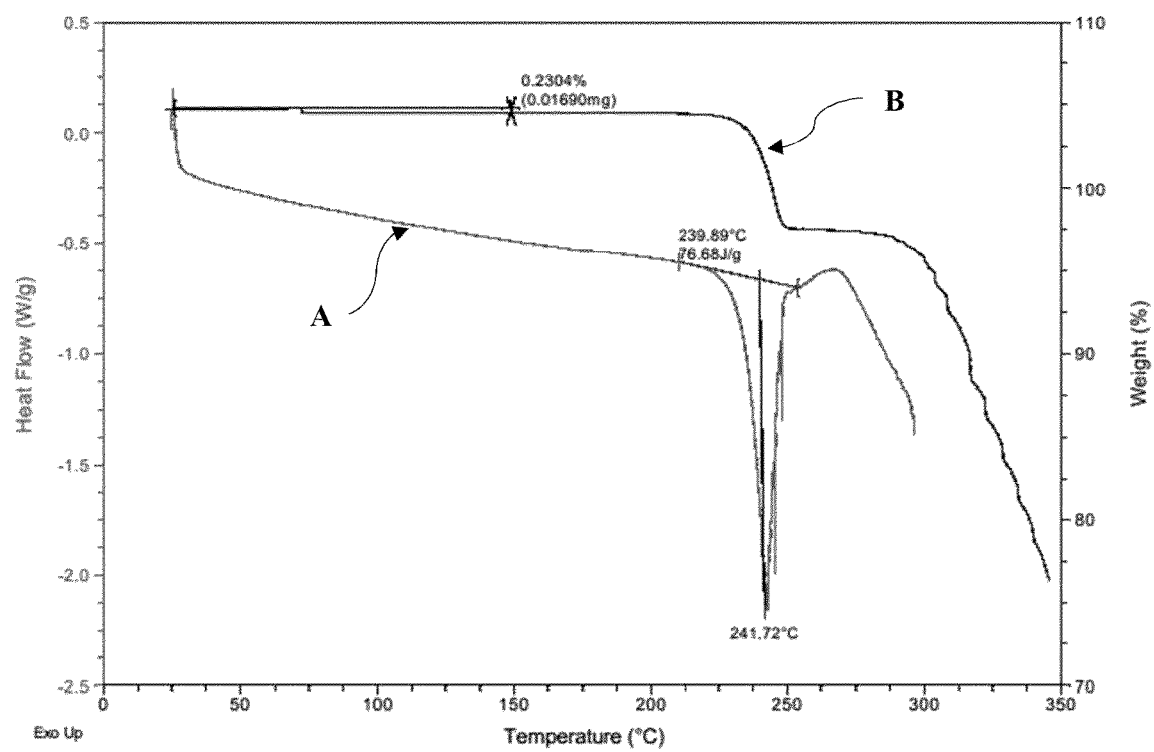

FIG. 3B provides a combined DSC (A) and TGA-IR (B) thermogram of Form A of Formula (I) prepared in Example 3 depicting heat flow (W/g)(y-axis) and weight (%)(y-axis) and temperature (° C.)(x-axis).

Figure 3C:
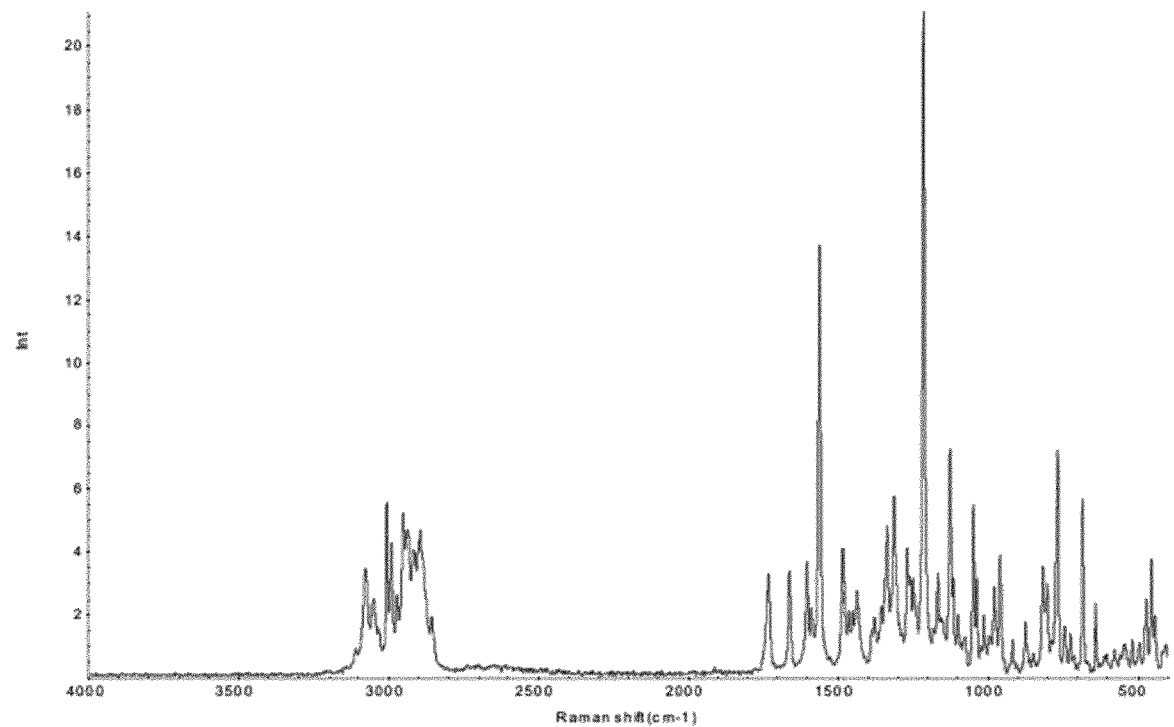

FIG. 3C provides s FTIR spectrum of Form A of Formula (I) prepared in Example 3 depicting intensity (counts)(y-axis) and Raman shift (cm$^{-1}$)(x-axis).

Figure 4A:
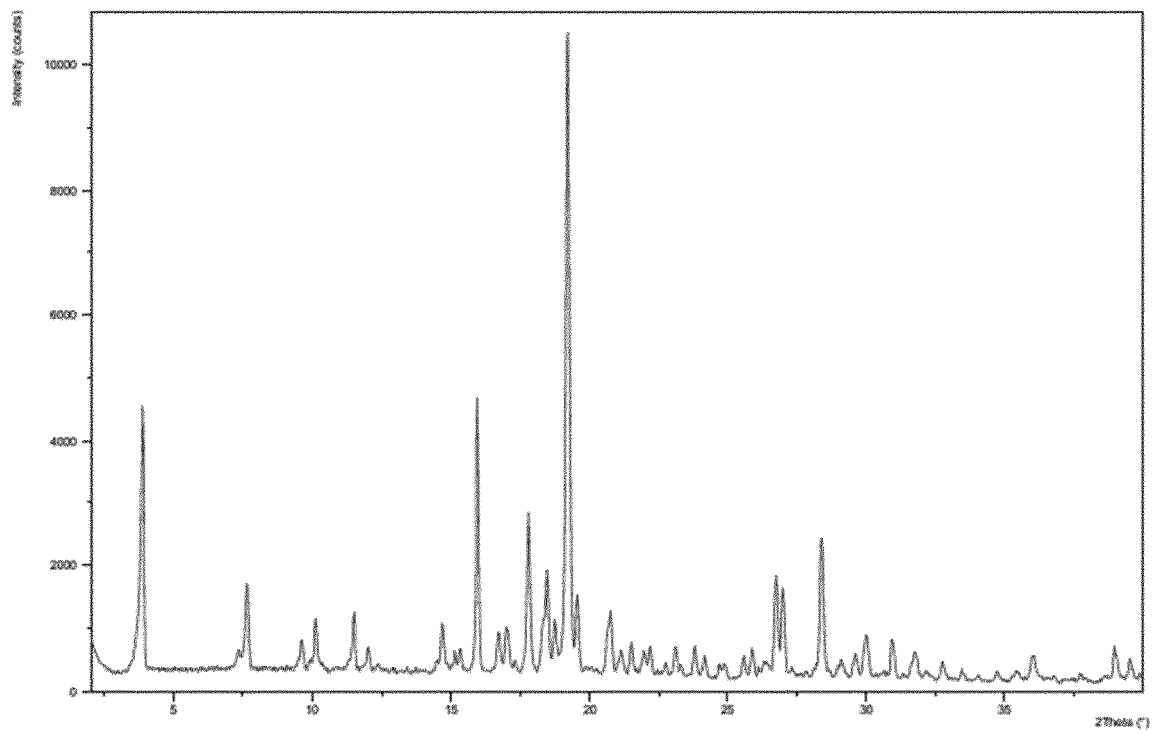

FIG. 4A provides a XRPD pattern of Form C of Formula (I) prepared in Example 3 depicting intensity (counts)(y-axis) and 2-theta (° 2Θ)(x-axis).

Figure 4B:
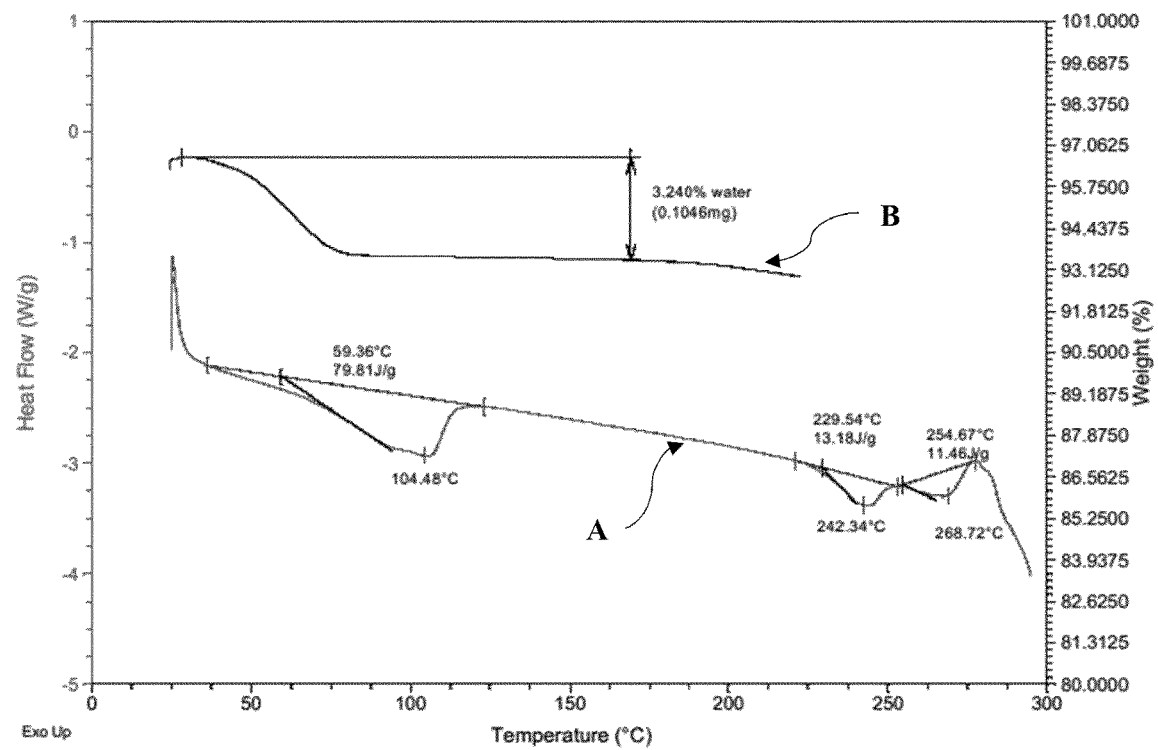

FIG. 4B provides a combined DSC (A) and TGA-IR (B) thermogram of Form C of Formula (I) prepared in Example 3 depicting heat flow (W/g)(y-axis) and weight (%)(y-axis) and temperature (° C.)(x-axis).

Figure 4C:
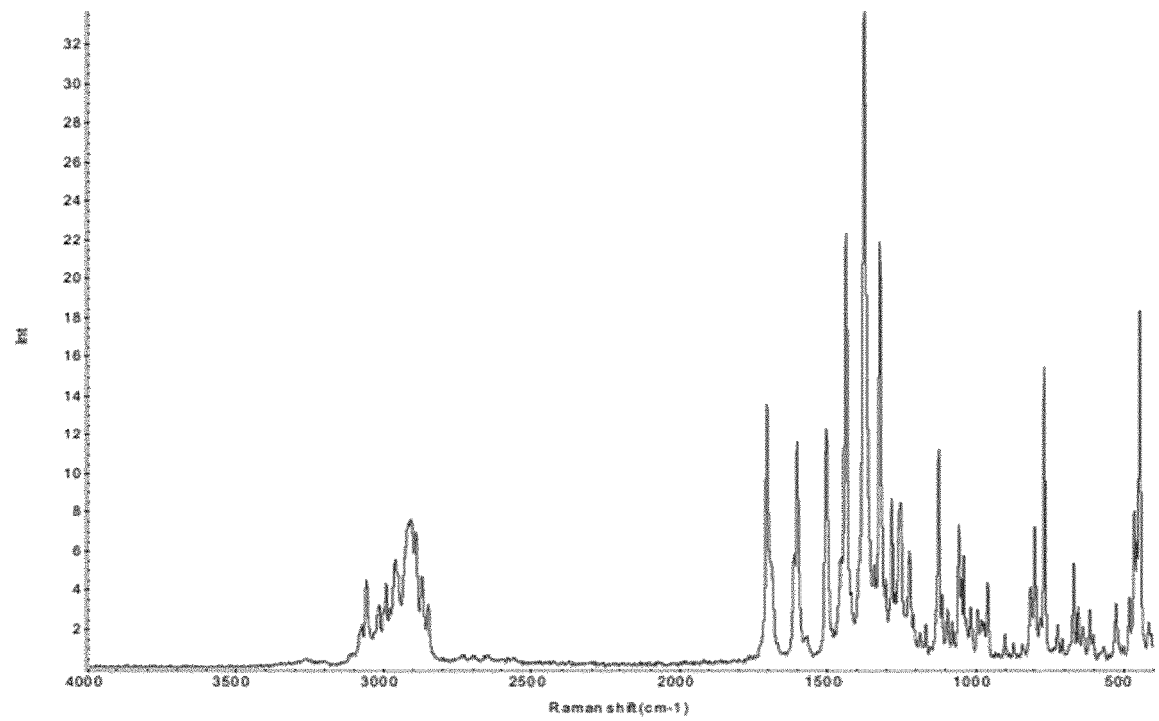

FIG. 4C provides s FTIR spectrum of Form C of Formula (I) prepared in Example 3 depicting intensity (counts)(y-axis) and Raman shift (cm$^{-1}$)(x-axis).

Figure 5A:
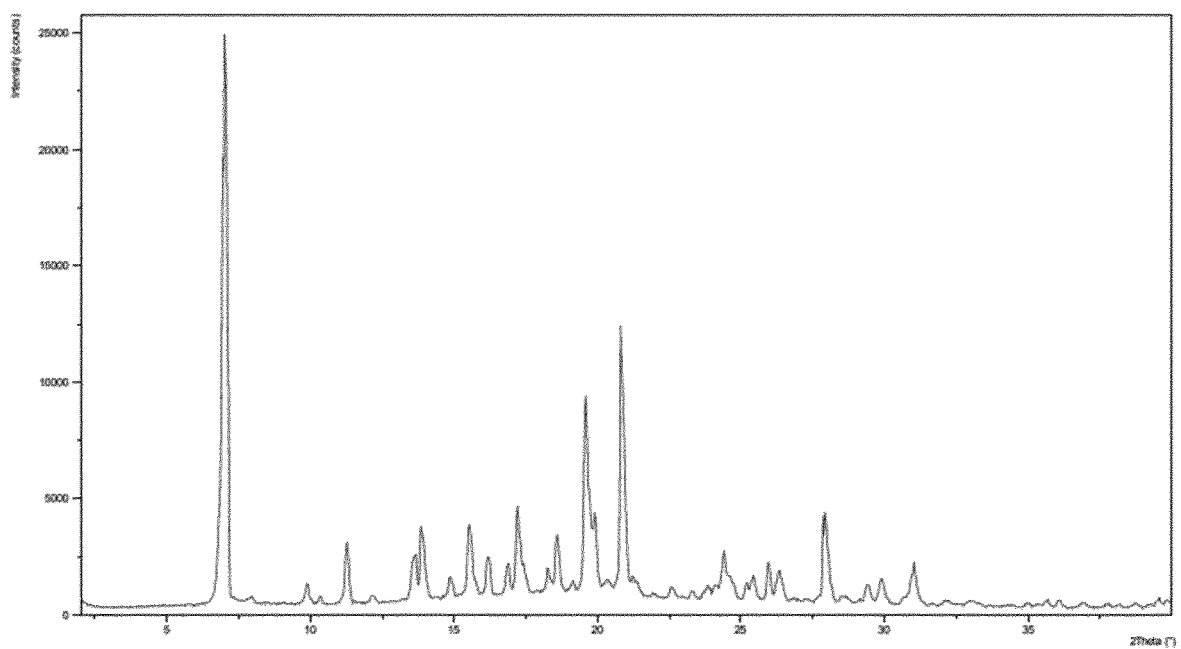

FIG. 5A provides a XRPD pattern of Form D of Formula (I) prepared in Example 3 depicting intensity (counts)(y-axis) and 2-theta (° 2Θ)(x-axis).

Figure 5B:
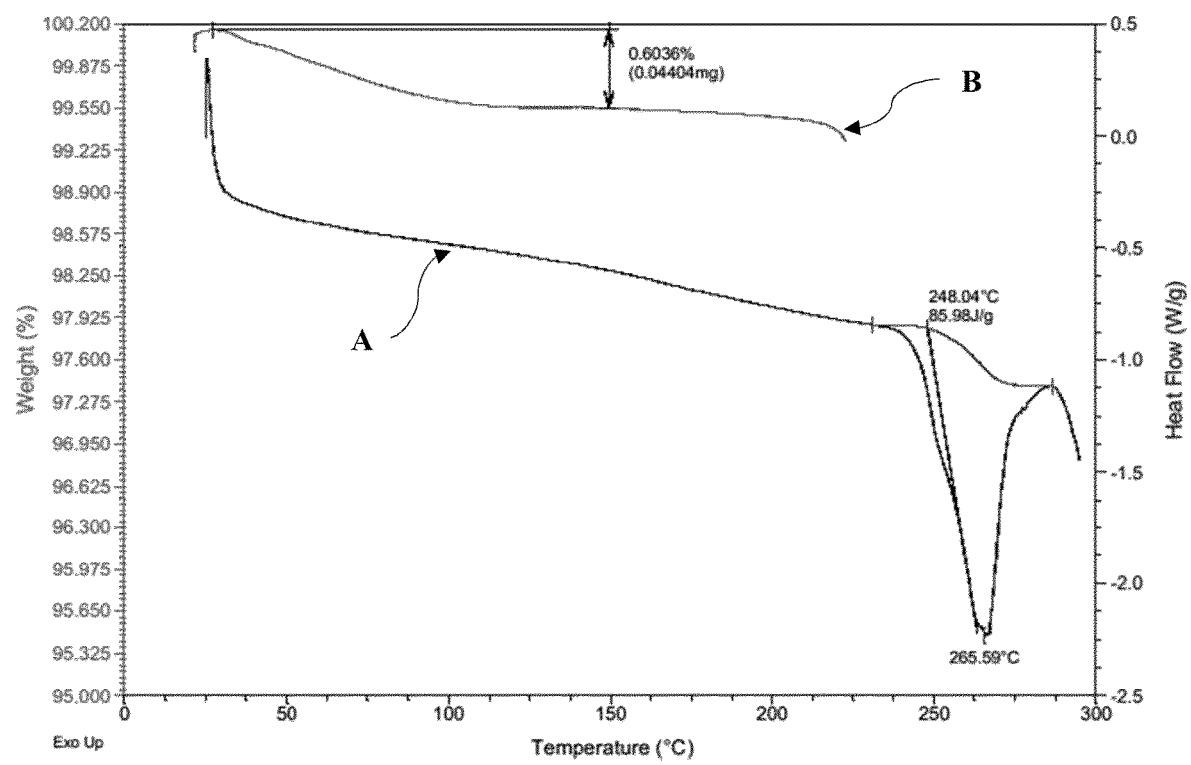

FIG. 5B provides a combined DSC (A) and TGA-IR (B) thermogram of Form D of Formula (I) prepared in Example 3 depicting heat flow (W/g)(y-axis) and weight (%)(y-axis) and temperature (° C.)(x-axis).

Figure 5C:
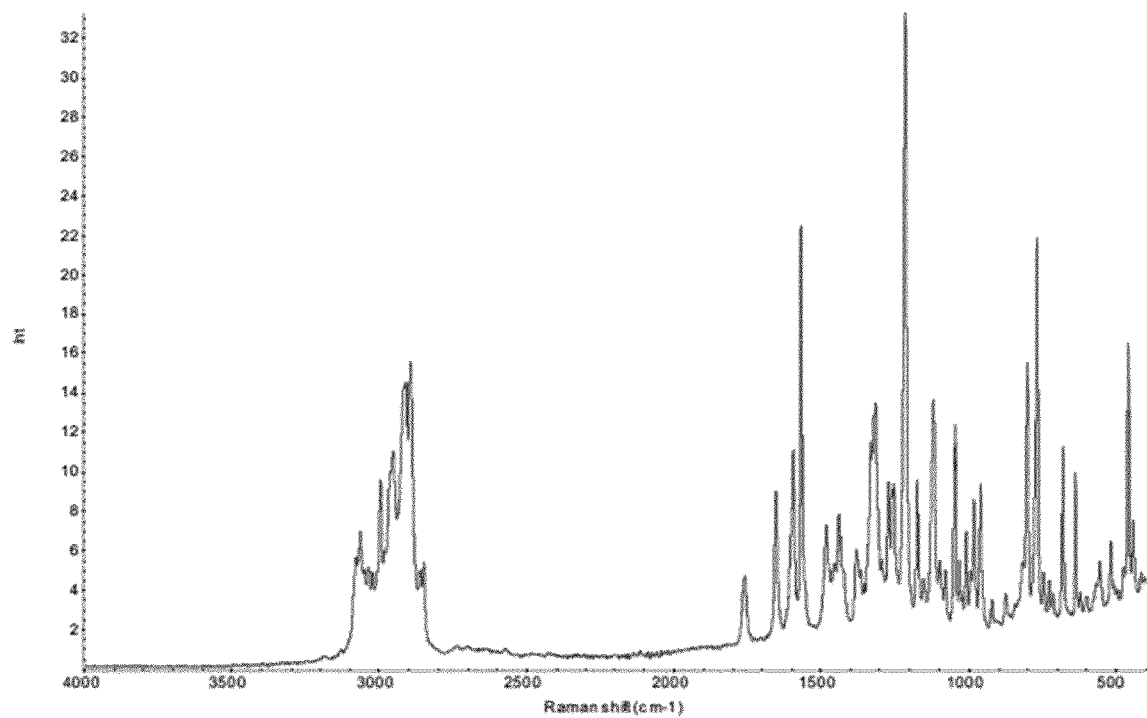

FIG. 5C provides s FTIR spectrum of Form D of Formula (I) prepared in Example 3 depicting intensity (counts)(y-axis) and Raman shift (cm$^{-1}$)(x-axis).

Figure 6:
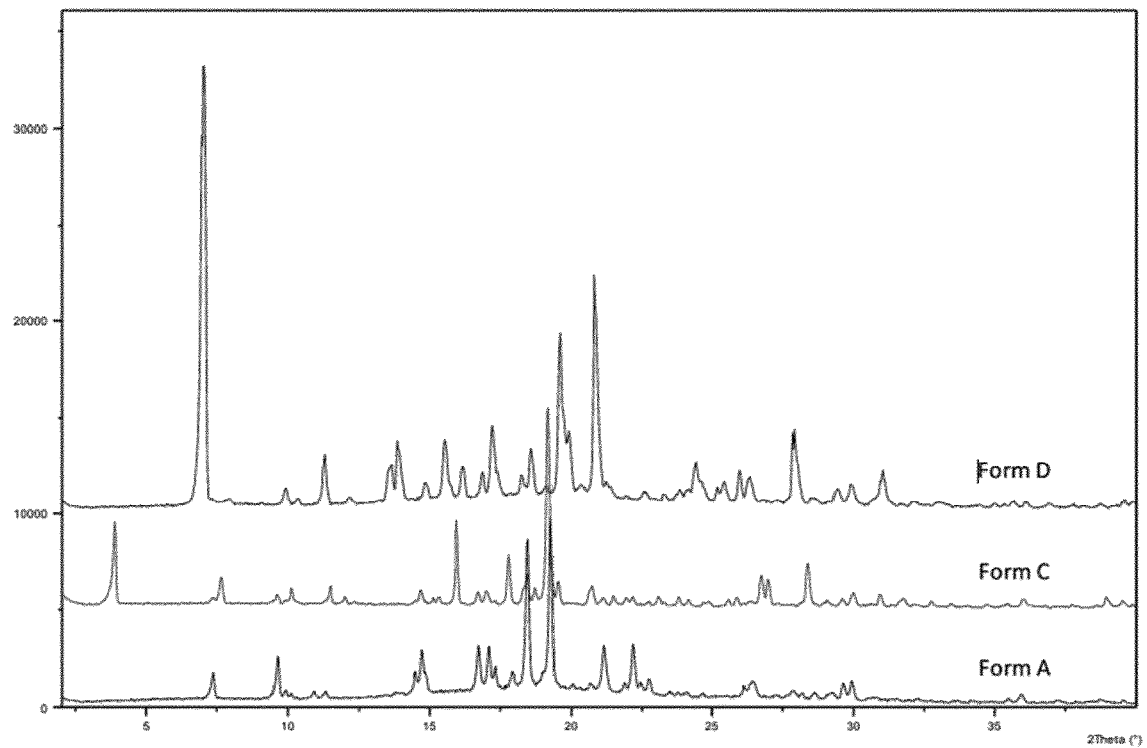

FIG. 6 provides an overlay of the XRPD patterns of Form A, C, and D of Formula (I) prepared in Example 3 depicting intensity (counts)(y-axis) and 2-theta (° 2Θ)(x-axis).

Figure 7A:
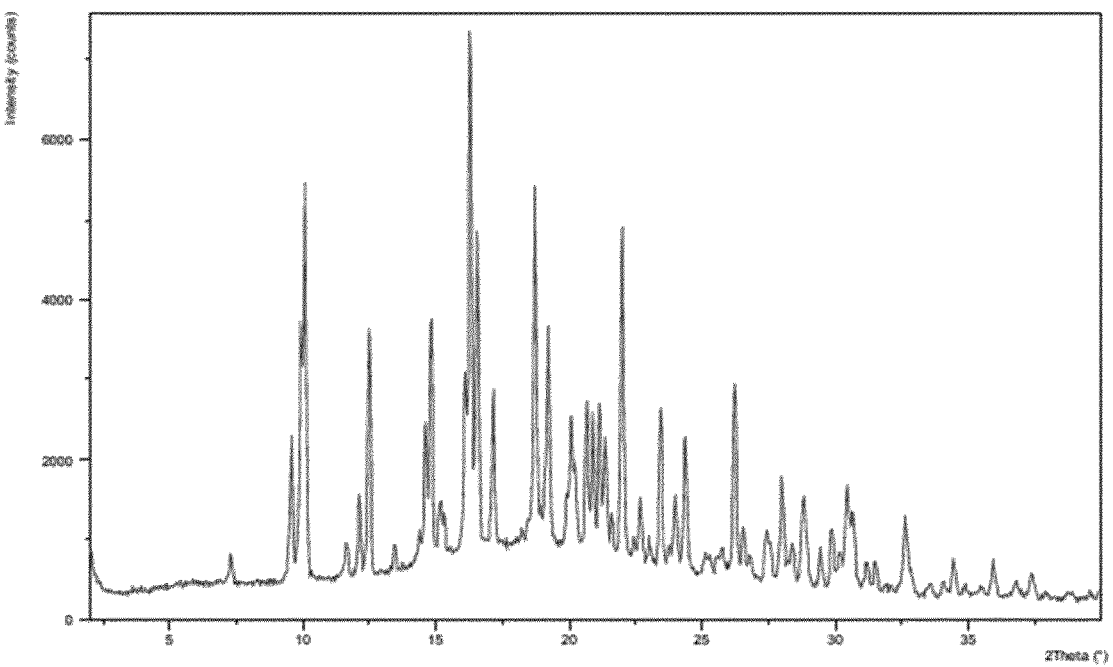

FIG. 7A provides a XRPD pattern of Form E of Formula (I) prepared in Example 3 depicting intensity (counts)(y-axis) and 2-theta (° 2Θ)(x-axis).

Figure 7B:
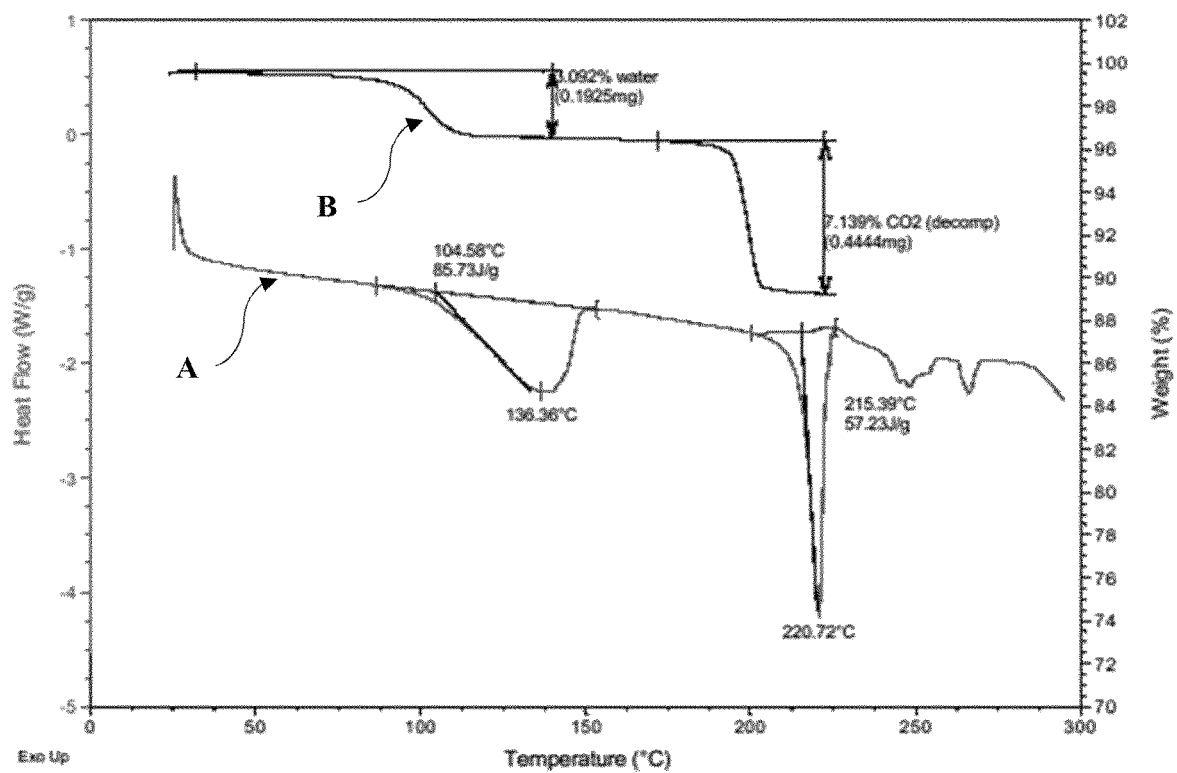

FIG. 7B provides a combined DSC (A) and TGA-IR (B) thermogram of Form E of Formula (I) prepared in Example 3 depicting heat flow (W/g)(y-axis) and weight (%)(y-axis) and temperature (° C.)(x-axis).

Figure 7C:
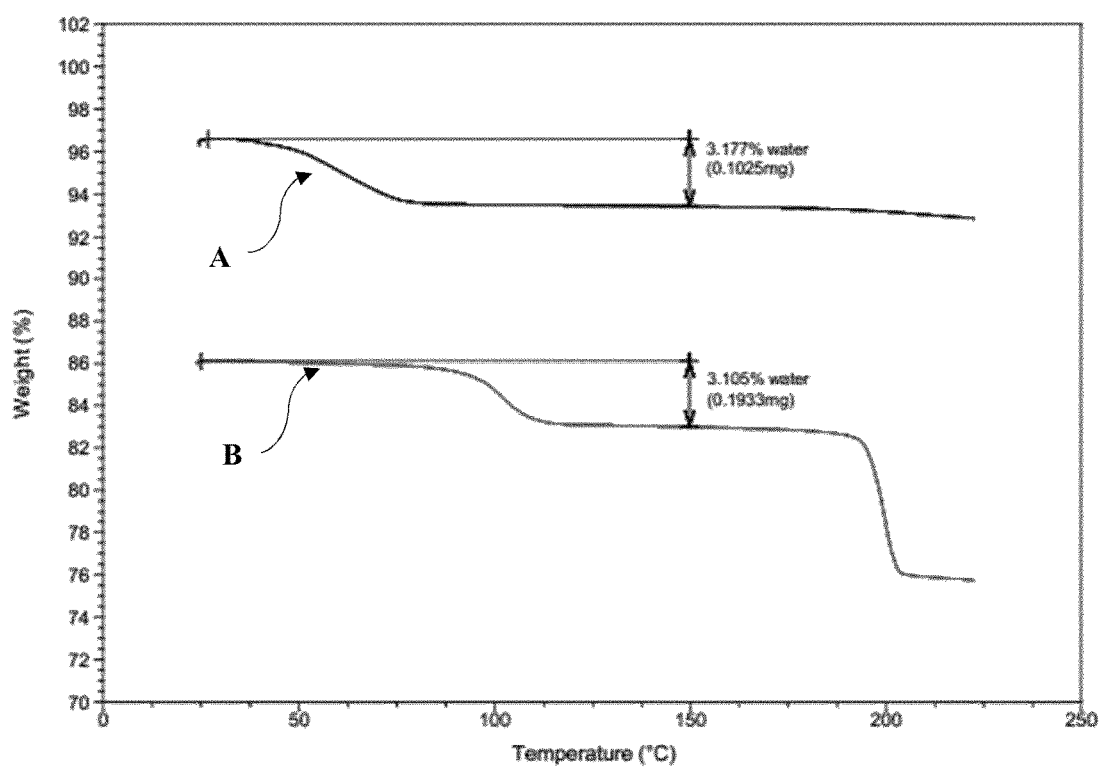

FIG. 7C provides a comparative TGA-IR thermogram of Form C (A) and Form E (B) of Formula (I) prepared in Example 3 depicting weight (%)(y-axis) and temperature (° C.)(x-axis).

Figure 7D:
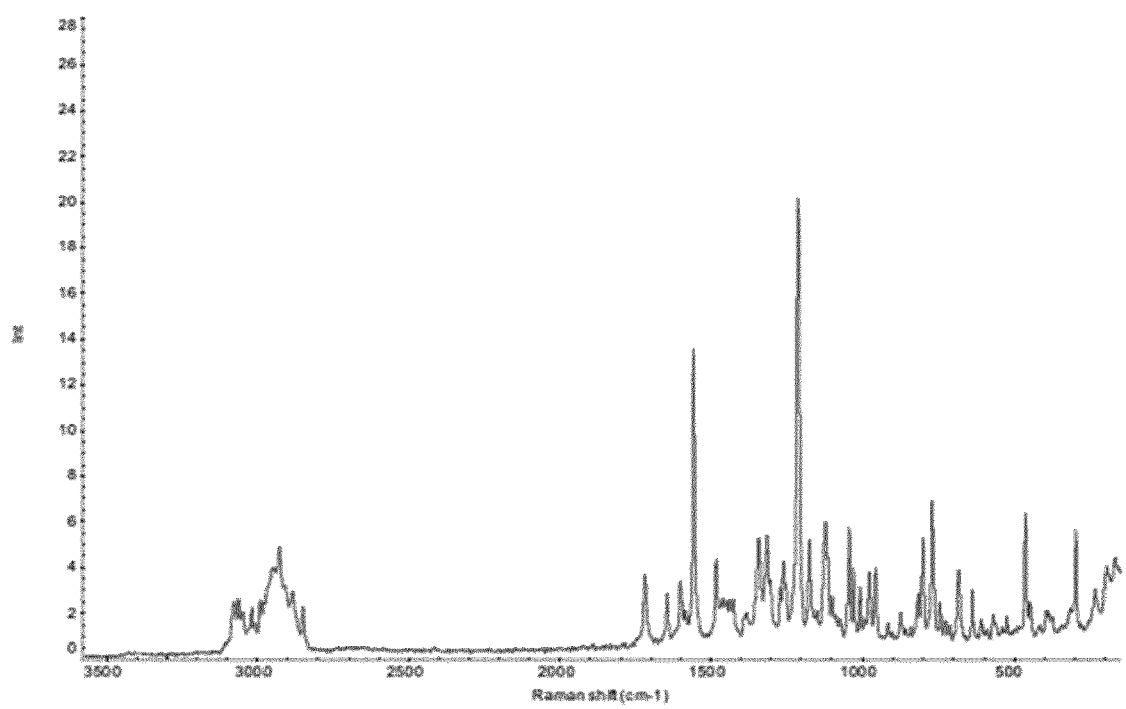

FIG. 7D provides a FTIR spectrum of Form E of Formula (I) prepared in Example 3 depicting intensity (counts)(y-axis) and Raman shift (cm$^{-1}$)(x-axis).

Figure 8A:
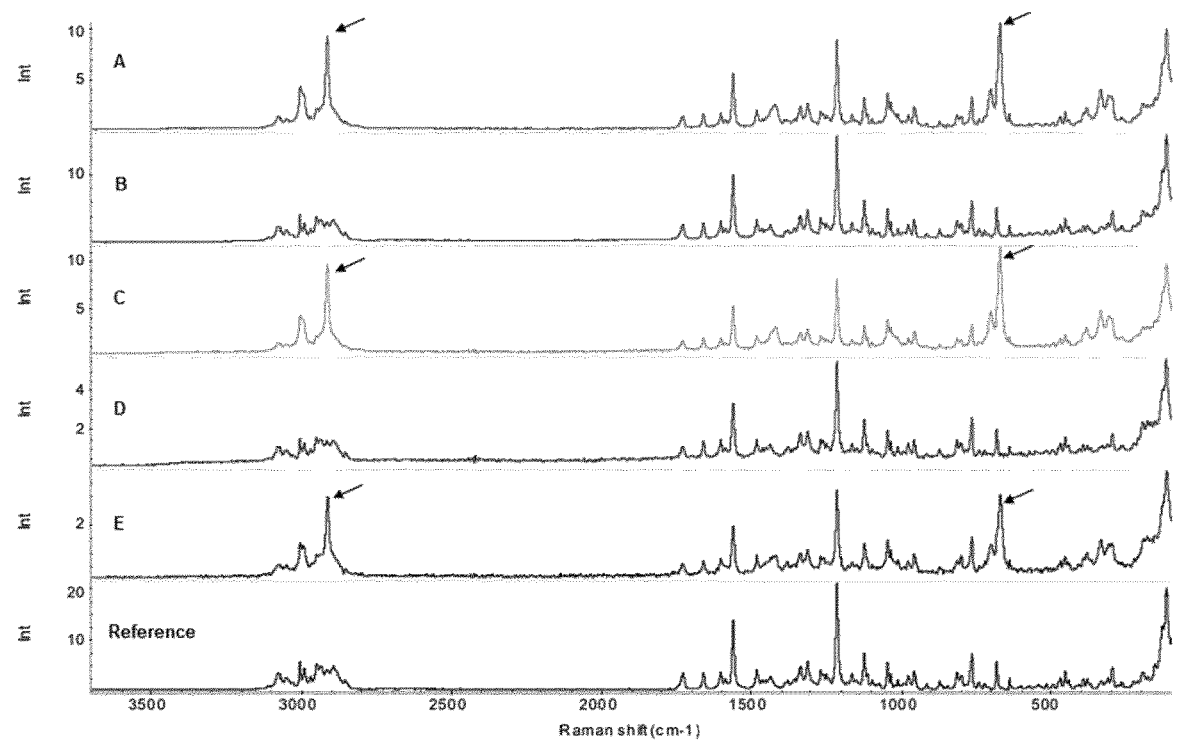

FIG. 8A provides multiple FTIR spectra showing results of the ripening study in Example 5 depicting intensity (counts)(y-axis) and Raman shift (cm$^{-1}$)(x-axis) of Form A, C, and D of in DMSO (A); Form A, C, and D in MeOH (B); Form A, C, and D in 77% DMSO/water (C); Form A, C, and D in 91% acetone/water (D); and Form A, C, and D in 83% water/DMSO (E); wherein black arrows indicate peaks for DMSO.

Figure 8B:
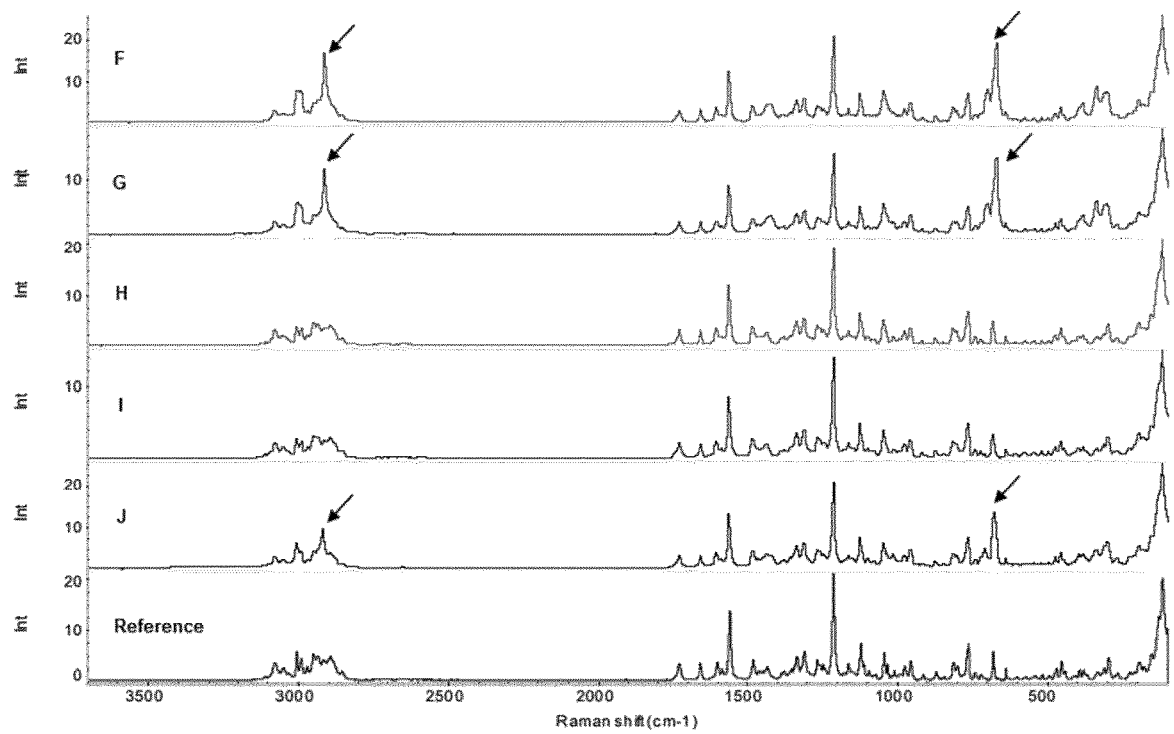

FIG. 8B provides multiple FTIR spectra showing results of the ripening study in Example 5 depicting intensity (counts)(y-axis) and Raman shift (cm$^{-1}$)(x-axis) of Form A and Form E in DMSO (F); Form A and Form E in MeOH (G); Form A and Form E in 77% DMSO/water (H); Form A and Form E in 91% acetone/water (I); and Form A and Form E in 83% water/DMSO (J); wherein black arrows indicate peaks for DMSO.

4. DETAILED DESCRIPTION

Provided herein are novel crystalline forms of the compound of Formula (I):

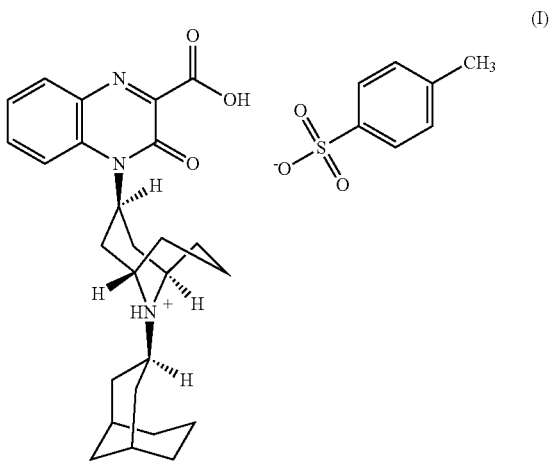

The compound of Formula (I) can be prepared by methods such as those described herein. The crystalline forms of Formula (I) can include, e.g., solvates, hydrates (e.g., monohydrates, dihydrates, etc.), and non-solvated or anhydrous forms of Formula (I). The crystalline forms of Formula (I) can include, e.g., crystalline forms A, B, C, D, and E provided herein.

In one embodiment, the present invention provides the Form A crystal-form of Formula (I). In some embodiments, Form A can be obtained by crystallization and recrystallization methods as described herein below.

A representative XRPD pattern of Form A of Formula (I) is provided in FIG. 3A. In some embodiments, Form A of Formula (I) has an XRPD pattern that is substantially similar to the pattern displayed in FIG. 3A.

Representative thermal characteristics of Form A of Formula (I) are shown in FIG. 3B. A representative DSC thermogram, presented as A in FIG. 3B, exhibits a composite endotherm at about 239.9° C. occurring with decomposition. A representative TGA thermogram, presented as B in FIG. 3B, exhibits a mass loss of less than about 0.2% weight loss from 25-150° C. These thermal data indicate that Form A of Formula (I) does not contain substantial amounts of either water or solvent in the crystal lattice.

In an embodiment, the present invention provides a crystalline form of Formula (I) that produces a powder X-ray diffraction spectrum comprising peaks at diffraction angles (2Θ±0.2°) of 18.5 and 19.3. In another embodiment, the crystalline form of Formula (I) may further comprise peaks at diffraction angles (2Θ±0.2°) of 21.1 and 22.2. In another embodiment, the crystalline form of Formula (I) may further comprise peaks at diffraction angles (2Θ±0.2°) of 7.4, 9.6, 14.7, 16.7, and 17.1. In another embodiment, the present invention provides a crystalline form of Formula (I) that produces a powder X-ray diffraction spectrum comprising peaks at diffraction angles (2Θ±0.2°) of 7.4, 9.6, 14.7, 16.7, 17.1, 18.5, 19.3, 21.1, and 22.2.

In an embodiment, the present invention provides a crystalline form of Formula (I) that produces a powder X-ray diffraction spectrum comprising peaks at diffraction angles (2Θ±0.2°) of 6.8 and 7.0. In another embodiment, the crystalline form of Formula (I) may further comprise peaks at diffraction angles (2Θ±0.2°) of 20.7 and 20.9. In another embodiment, the crystalline form of Formula (I) may further comprise peaks at diffraction angles (2Θ±0.2°) of 17.2, 19.6, and 27.8. In another embodiment, the present invention provides a crystalline form of Formula (I) that produces a powder X-ray diffraction spectrum comprising peaks at diffraction angles (2Θ±0.2°) of 6.8, 7.0, 13.7, 15.5, 17.1, 17.2, 18.5, 18.6, 19.5, 19.6, 20.7, 20.9, 27.8, 28.0.

In an embodiment, the present invention provides a crystalline form of Formula (I) that produces a powder X-ray diffraction spectrum comprising peaks at diffraction angles (2Θ±0.2°) of 16.0 and 19.2. In another embodiment, the crystalline form of Formula (I) may further comprise peaks at diffraction angles (2Θ±0.2°) of 3.9 and 7.6. In another embodiment, the crystalline form of Formula (I) may further comprise peaks at diffraction angles (2Θ±0.2°) of 18.0, 26.7, 27.0, and 28.4. In another embodiment, the present invention provides a crystalline form of Formula (I) that produces a powder X-ray diffraction spectrum comprising peaks at diffraction angles (2Θ±0.2°) of 3.9, 7.6, 16.0, 18.0, 19.2, 26.7, 27.0, 28.4.

In an embodiment, the present invention provides a crystalline form of Formula (I) that produces a powder X-ray diffraction spectrum comprising peaks at diffraction angles (2Θ±0.2°) of 7.1 and 20.8. In another embodiment, the crystalline form of Formula (I) may further comprise peaks at diffraction angles (2Θ±0.2°) of 17.2 and 19.6. In another embodiment, the crystalline form of Formula (I) may further comprise peaks at diffraction angles (2Θ±0.2°) of 13.9, 15.5, and 27.9. In another embodiment, the present invention provides a crystalline form of Formula (I) that produces a powder X-ray diffraction spectrum comprising peaks at diffraction angles (2Θ±0.2°) of 7.1, 13.9, 15.5, 17.2, 19.6, 19.9, 20.8, 27.9.

In an embodiment, the present invention provides a crystalline form of Formula (I) that produces a powder X-ray diffraction spectrum comprising peaks at diffraction angles (2Θ±0.2°) of 10.1 and 16.3. In another embodiment, the crystalline form of Formula (I) may further comprise peaks at diffraction angles (2Θ±0.2°) of 18.7 and 22.0. In another embodiment, the crystalline form of Formula (I) may further comprise peaks at diffraction angles (2Θ±0.2°) of 12.5, 14.8, 23.4, and 26.2. In another embodiment, the present invention provides a crystalline form of Formula (I) that produces a powder X-ray diffraction spectrum comprising peaks at diffraction angles (2Θ±0.2°) of 10.1, 12.5, 14.8, 16.3, 16.6, 18.7, 22.0, 23.4, 26.2.

In an embodiment, the present invention provides a crystalline compound of Formula (I), wherein at least about 90% by wt. of the crystalline compound of Formula (I) is crystalline Form A, which produces a powder X-ray diffraction spectrum comprising at least three peaks at diffraction angles (2Θ±0.2°) selected from 7.4, 9.6, 14.7, 16.7, 17.1, 18.5, 19.3, 21.1, and 22.2. In another embodiment, at least about 95% by wt. of crystalline Formula (I) is crystalline Form A.

In an embodiment, the present invention provides a crystalline compound of Formula (I), wherein at least about 90% by wt. of the crystalline compound of Formula (I) is crystalline Form B, which produces a powder X-ray diffraction spectrum comprising at least three peaks at diffraction angles (2Θ±0.2°) selected from 6.8, 7.0, 13.7, 15.5, 17.1, 17.2, 18.5, 18.6, 19.5, 19.6, 20.7, 20.9, 27.8, and 28.0. In another embodiment, at least about 95% by wt. of the crystalline Formula (I) is crystalline Form B.

In an embodiment, the present invention provides a crystalline compound of Formula (I), wherein at least about 90% by wt. of the total amount of the crystalline compound of Formula (I) is crystalline Form C, which produces a powder X-ray diffraction spectrum comprising at least three peaks at diffraction angles (2Θ±0.2°) selected from 3.9, 7.6, 16.0, 18.0, 19.2, 26.7, 27.0, and 28.4. In another embodiment, at least about 95% by wt. of the total amount of crystalline forms of Formula (I) is present as the claimed crystalline Form C.

In an embodiment, the present invention provides a crystalline compound of Formula (I), wherein at least about 90% by wt. of the crystalline compound of Formula (I) is crystalline Form D, which produces a powder X-ray diffraction spectrum comprising at least three peaks at diffraction angles (2Θ±0.2°) selected from 7.1, 13.9, 15.5, 17.2, 19.6, 19.9, 20.8, and 27.9. In another embodiment, at least about 95% by wt. of the total amount of the crystalline compound of Formula (I) is crystalline Form D.

In an embodiment, the present invention provides a crystalline compound of Formula (I), wherein at least about 90% by wt. of the crystalline compound of Formula (I) is crystalline Form E, which produces a powder X-ray diffraction spectrum comprising at least three peaks at diffraction angles (2Θ±0.2°) selected from 10.1, 12.5, 14.8, 16.3, 16.6, 18.7, 22.0, 23.4, and 26.2. In another embodiment, at least about 95% by wt. of the total amount of the crystalline compound of Formula (I) is crystalline Form E.

In certain embodiments, the invention provides bulk amounts of a crystalline or amorphous form of a compound of Formula (I). In an embodiment, a bulk amount of a crystalline compound of Formula (I) may include greater than about 1 kg, greater than about 10 kg, or greater than about 100 kg. In another embodiment, a bulk amount of a crystalline compound of Formula (I) may include from about 1 kg to about 1000 kg, from about 10 kg to about 1000 kg, from about 100 kg to about 1000 kg, from about 1 kg to about 100 kg; from about 10 kg to about 100 kg; or from about 1 kg to about 10 kg.

4.1.1. Definitions

"About" refers to an approximate value, such as a value ±0.5% of the recited value. For example, a crystalline form having a crystalline purity of about 90% by wt. is about 89.5% to 90.5% by wt.

A "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject, e.g., a human.

"Treating" with regard to a subject, e.g., a human, refers to improving at least one symptom of the subject's disorder. Treating includes curing, improving, or at least partially ameliorating the disorder.

A "disorder" is used in this disclosure to mean, and is used interchangeably with, the terms disease, condition, or illness, unless otherwise indicated.

The terms "administer", "administering", or "administration" as used in this disclosure refers to either directly administering a disclosed compound or pharmaceutical composition thereof to a subject, e.g., a human.

The term "effective amount", when used in connection with methods for treating or preventing a disorder by administering a disclosed compound, refers to an amount of the compound administered to a subject, e.g., a human, that provides a therapeutic effect.

The term "crystalline" and related terms used herein, when used to describe a substance, component or product, means that the substance, component or product is substantially crystalline as determined by X-ray diffraction, microscopy, polarized microscopy, or other known analytical procedure known to those skilled in the art.

The term "polymorph," as used herein, refers to crystalline forms of a compound having different unit cell structures in crystals, originating from a variety of molecular conformations and molecular packing. Polymorphs of a single compound can have one or more different chemical, physical, mechanical, electrical, thermodynamic, and/or biological properties from each other. Differences in physical properties exhibited by polymorphs can affect pharmaceutical parameters such as storage stability, compressibility, density (important in composition and product manufacturing), dissolution rates (an important factor in determining bio-availability), solubility, melting point, chemical stability, physical stability, powder flowability, water sorption, compaction, and particle morphology. Differences in stability can result from changes in chemical reactivity (e.g., differential oxidation, such that a dosage form discolors more rapidly when comprised of one polymorph than when comprised of another polymorph), or mechanical changes (e.g., crystal changes on storage as a kinetically favored polymorph converts to a thermodynamically more stable polymorph) or both (e.g., one polymorph is more hygroscopic than the other). As a result of solubility/dissolution differences, some transitions affect potency and/or toxicity.

In addition, the physical properties of the crystal may be important in processing; for example, one polymorph might be more likely to form solvates or might be difficult to filter and wash free of impurities (i.e., particle shape and size distribution might be different between one polymorph relative to the other). As used herein, "amorphous" refers to a noncrystalline form of a compound which may be a solid state form of the compound or a solubilized form of the compound. For example, "amorphous" refers to a compound without a regularly repeating arrangement of molecules or external face planes.

The term "anhydrous," as used herein, refers to a crystalline form having a water content of less than or equal to about 0.1, 0.3, 0.5, 1, 2, 3, 4, 5, 6, 7, 8, 9, or 10% by weight relative to the total weight of the composition. In some instances, anhydrous crystalline forms can be referred to as non-solvates.

The term "solvate" as used herein refers to a crystalline form of a compound of Formula (I), such as a polymorph form of the compound, where the crystal lattice comprises one or more solvents of crystallization. Examples of solvents include, but are not limited to, water, MeOH, EtOH, and AcOH. A solvate wherein water is the solvent molecule is typically referred to as a "hydrate". Hydrates include compositions containing stoichiometric amounts of water, as well as compositions containing variable amounts of water.

As used herein, the term "substantially pure crystalline form" means a crystalline form having a crystalline purity wherein no other crystalline form is detectable by using a PANalytical X'Pert Pro diffractometer using Ni-filtered Cu Kα (45 kV/40 mA) radiation or an equivalent instrument known to those of skill in the art.

The crystalline forms of the instant invention can be characterized using Single Crystal Data, Powder X-Ray Diffraction ("PXRD" or "XRPD"), Differential Scanning calorimetry ("DSC"), Thermogravimetric Analysis ("TGA"), and Raman Spectroscopy. It is to be understood that numerical values described and claimed herein are approximate. Variation within the values may be attributed to equipment calibration, equipment errors, purity of the materials, crystals size, and sample size, among other factors. In addition, variation may be possible while still obtaining the same result. For example, X-ray diffraction values are generally accurate to within ±0.2 degrees and intensities (including relative intensities) in an X-ray diffraction pattern may fluctuate depending upon measurement conditions employed. Similarly, DSC results are typically accurate to within about 2° C. Consequently, it is to be understood that the crystalline forms of the instant invention are not limited to the crystalline forms that provide characterization patterns (i.e., one or more of the PXRD, DSC, and TGA) completely identical to the characterization patterns depicted in the accompanying Figures disclosed herein. Any crystalline forms that provide characterization patterns substantially the same (e.g., 2Θ±0.2°) as those described in the accompanying Figures fall within the scope of the present invention. The ability to ascertain substantially the same characterization patterns is within the purview of one of ordinary skill in the art.

Pharmaceutical compositions and single unit dosage forms comprising a crystalline form of the invention are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient.

The composition, shape, and type of dosage forms of the invention will typically vary depending on their use. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1995).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including but not limited to the way in which the dosage form will be administered to a patient. For example, oral dosage forms such as tablets may contain excipients not suited for use in parenteral dosage forms. The suitability of a particular excipient may also depend on the specific active ingredients in the dosage form.

4.1.2. Crystalline Forms

Form A

One such crystalline form of Formula (I) is known as Form A. In some embodiments, Form A is a non-solvated crystalline form of Formula (I). In some embodiments, Form A is an anhydrous crystalline form of Formula (I).

In certain embodiments, the Form A is characterized by an X-Ray powder diffraction pattern, obtained with Ni-filtered Cu Kα (45 kV/40 mA) radiation, comprising at least two or three peaks at diffraction angles (2Θ±0.2°) selected from 7.4, 9.6, 14.7, 16.7, 17.1, 18.5, 19.3, 21.1, and 22.2. For example, see FIG. 3A.

In some embodiments, the Form A is characterized by an X-Ray powder diffraction pattern comprising at least characteristic peaks at a diffraction angle (2Θ±0.2°) of 18.5 and 19.3. In some embodiments, the Form A is characterized by an X-Ray powder diffraction pattern comprising at least characteristic peaks at a diffraction angle (2Θ±0.2°) of 18.5, 19.3, and 21.1. In some embodiments, the Form A is characterized by an X-Ray powder diffraction pattern comprising at least characteristic peaks at a diffraction angle (2Θ±0.2°) of 18.5, 19.3, and 22.2. In some embodiments, the Form A is characterized by an X-Ray powder diffraction pattern comprising at least characteristic peaks at a diffraction angle (2Θ±0.2°) of 17.1, 18.5 and 19.3. In some embodiments, the Form A is characterized by an X-Ray powder diffraction pattern comprising at least characteristic peaks at a diffraction angle (2Θ±0.2°) of 16.7, 18.5 and 19.3. In some embodiments, the Form A is characterized by an X-Ray powder diffraction pattern comprising at least characteristic peaks at a diffraction angle (2Θ±0.2°) of 14.7, 18.5 and 19.3. In some embodiments, the Form A is characterized by an X-Ray powder diffraction pattern comprising at least characteristic peaks at a diffraction angle (2Θ±0.2°) of 9.6, 18.5 and 19.3. In some embodiments, the Form A is characterized by an X-Ray powder diffraction pattern comprising at least characteristic peaks at a diffraction angle (2Θ±0.2°) of 18.5, 19.3, 21.1, and 22.2. In some embodiments, the Form A is characterized by an X-Ray powder diffraction pattern comprising at least characteristic peaks at a diffraction angle (2Θ±0.2°) of 16.7, 17.1, 18.5, 19.3, 21.1, and 22.2. For example, in some embodiments, the Form A is characterized by an X-Ray powder diffraction pattern comprising at least characteristic peaks at a diffraction angle (2Θ±0.2°) of 9.6, 14.7, 16.7, 17.1, 18.5, 19.2, 21.1, and 22.2.

In certain embodiments, the Form A is characterized by an X-Ray powder diffraction pattern, obtained with Ni-filtered Cu Kα (45 kV/40 mA) radiation, comprising at least two or three d-spacing values (d-spacing±0.2 Å) selected from 12.0, 9.2, 6.0, 5.3, 5.2, 4.8, 4.6, 4.2, and 4.0.

In some embodiments, the Form A is characterized by an X-Ray powder diffraction pattern comprising at least d-spacing values (d-spacing±0.2 Å) at 4.8 and 4.6. In some embodiments, the Form A is characterized by an X-Ray powder diffraction pattern comprising at least d-spacing values (d-spacing±0.2 Å) at 4.8, 4.6, and 4.2. In some embodiments, the Form A is characterized by an X-Ray powder diffraction pattern comprising at least d-spacing values (d-spacing±0.2 Å) at 4.8, 4.6, and 4.0. In some embodiments, the Form A is characterized by an X-Ray powder diffraction pattern comprising at least d-spacing values (d-spacing±0.2 Å) at 5.2, 4.8 and 4.6. In some embodiments, the Form A is characterized by an X-Ray powder diffraction pattern comprising at least d-spacing values (d-spacing±0.2 Å) at 5.3, 4.8 and 4.6. In some embodiments, the Form A is characterized by an X-Ray powder diffraction pattern comprising at least d-spacing values (d-spacing±0.2 Å) at 6.0, 4.8 and 4.6. In some embodiments, the Form A is characterized by an X-Ray powder diffraction pattern comprising at least d-spacing values (d-spacing±0.2 Å) at 9.6, 4.8 and 4.6. In some embodiments, the Form A is characterized by an X-Ray powder diffraction pattern comprising at least d-spacing values (d-spacing±0.2 Å) at 4.8, 4.6, 4.2, and 4.0. In some embodiments, the Form A is characterized by an X-Ray powder diffraction pattern comprising at least d-spacing values (d-spacing±0.2 Å) at 6.0, 5.3, 5.2, 4.8, and 4.6. For example, in some embodiments, the Form A is characterized by an X-Ray powder diffraction pattern comprising at least d-spacing values (d-spacing±0.2 Å) at 9.2, 6.0, 5.3, 5.2, 4.8, 4.6, 4.2, and 4.0.

In some embodiments, the Form A is characterized by a differential scanning calorimetry (DSC) thermogram with an endothermic event ranging in temperature of from about 235° C. to about 250° C. with a peak temperature of about 241° C. In some embodiments, the endothermic event occurs with decomposition. In some embodiments, the endotherms are observed when using a scan rate of 15° C./min.

In some embodiments, the Form A is characterized by a thermogravimetric analysis (TGA-IR) thermogram with about a 0.2% weight loss event ranging in temperature of from about 25 to about 150° C. In some embodiments, the weight loss is observed when using a scan rate of 15° C./min.

Surprisingly, it was found that Form A is the most stable crystalline form of the compound of Formula (I). This was confirmed in ripening studies. It may thus be preferred to use the more stable crystalline form of the compound of Formula (I) in a pharmaceutical composition or dosage form. By using said form, the degradation or the modification of the pharmaceutical composition or dosage form can be avoided.

Form B

Another crystalline form of Formula (I) is known as Form B.

In certain embodiments, the Form B is characterized by an X-Ray powder diffraction pattern, obtained with Cu Kα (50 kV/300 mA) radiation, comprising at least two or three peaks at diffraction angles (2Θ±0.2°) selected from 6.8, 7.0, 13.7, 15.5, 17.1, 17.2, 18.5, 18.6, 19.5, 19.6, 20.7, 20.9, 27.8, and 28.0. For example, see FIG. 1.

In some embodiments, the Form B is characterized by an X-Ray powder diffraction pattern comprising at least characteristic peaks at a diffraction angle (2Θ±0.2°) of 6.8 and 7.0. In some embodiments, the Form B is characterized by an X-Ray powder diffraction pattern comprising at least characteristic peaks at a diffraction angle (2Θ±0.2°) of 6.8, 7.0, and 20.7. In some embodiments, the Form B is characterized by an X-Ray powder diffraction pattern comprising at least characteristic peaks at a diffraction angle (2Θ±0.2°) of 6.8, 7.0, and 20.9. In some embodiments, the Form B is characterized by an X-Ray powder diffraction pattern comprising at least characteristic peaks at a diffraction angle (2Θ±0.2°) of 6.8, 7.0, and 19.6. In some embodiments, the Form B is characterized by an X-Ray powder diffraction pattern comprising at least characteristic peaks at a diffraction angle (2Θ±0.2°) of 6.8, 7.0, and 17.2. In some embodiments, the Form B is characterized by an X-Ray powder diffraction pattern comprising at least characteristic peaks at a diffraction angle (2Θ±0.2°) of 6.8, 7.0, and 27.8. In some embodiments, the Form B is characterized by an X-Ray powder diffraction pattern comprising at least characteristic peaks at a diffraction angle (2Θ±0.2°) of 6.8, 7.0, 20.7, and 20.9. In some embodiments, the Form B is characterized by an X-Ray powder diffraction pattern comprising at least characteristic peaks at a diffraction angle (2Θ±0.2°) of 6.8, 7.0, 19.6, 20.7, and 20.9. In some embodiments, the Form B is characterized by an X-Ray powder diffraction pattern comprising at least characteristic peaks at a diffraction angle (2Θ±0.2°) of 6.8, 7.0, 17.2, 19.6, 20.7, and 20.9. For example, in some embodiments, the Form B is characterized by an X-Ray powder diffraction pattern comprising at least characteristic peaks at a diffraction angle (2Θ±0.2°) of 6.8, 7.0, 13.7, 15.5, 17.1, 17.2, 18.5, 18.6, 19.5, 19.6, 20.7, 20.9, 27.8, and 28.0.

In certain embodiments, the Form B is characterized by an X-Ray powder diffraction pattern, obtained with Cu Kα (50 kV/300 mA) radiation, comprising at least two or three d-spacing values (d-spacing±0.2 Å) selected from 12.9, 12.6, 6.4, 5.7, 5.2, 5.1, 4.8, 4.7, 4.6, 4.5, 4.3, 4.2, and 3.2.

In some embodiments, the Form B is characterized by an X-Ray powder diffraction pattern comprising at least d-spacing values (d-spacing±0.2 Å) at 12.9 and 12.6. In some embodiments, the Form B is characterized by an X-Ray powder diffraction pattern comprising at least d-spacing values (d-spacing±0.2 Å) at 12.9, 12.6, and 4.3. In some embodiments, the Form B is characterized by an X-Ray powder diffraction pattern comprising at least d-spacing values (d-spacing±0.2 Å) at 12.9, 12.6, and 4.2. In some embodiments, the Form B is characterized by an X-Ray powder diffraction pattern comprising at least d-spacing values (d-spacing±0.2 Å) at 12.9, 12.6, and 5.1. In some embodiments, the Form B is characterized by an X-Ray powder diffraction pattern comprising at least d-spacing values (d-spacing±0.2 Å) at 12.9, 12.6, and 3.2. In some embodiments, the Form B is characterized by an X-Ray powder diffraction pattern comprising at least d-spacing values (d-spacing±0.2 Å) at 12.9, 12.6, 4.3 and 4.2. In some embodiments, the Form B is characterized by an X-Ray powder diffraction pattern comprising at least d-spacing values (d-spacing±0.2 Å) at 12.9, 12.6, 4.5 and 5.1. In some embodiments, the Form B is characterized by an X-Ray powder diffraction pattern comprising at least d-spacing values (d-spacing±0.2 Å) at 12.9, 12.6, 4.3, 4.2, and 5.1. For example, in some embodiments, the Form B is characterized by an X-Ray powder diffraction pattern comprising at least d-spacing values (d-spacing±0.2 Å) at 12.9, 12.6, 6.4, 5.7, 5.2, 5.1, 4.8, 4.7, 4.6, 4.5, 4.3, 4.2, and 3.2.

Form C

Another crystalline form of Formula (I) is known as Form C. Form C is a monohydrate crystalline form of Formula (I).

In certain embodiments, the Form C is characterized by an X-Ray powder diffraction pattern, obtained with Ni-filtered Cu Kα (45 kV/40 mA) radiation, comprising at least two or three peaks at diffraction angles (2Θ±0.2°) selected from 3.9, 7.6, 16.0, 18.0, 19.2, 26.7, 27.0, and 28.4. For example, see FIG. 4A.

In some embodiments, the Form C is characterized by an X-Ray powder diffraction pattern comprising at least characteristic peaks a diffraction angle (2Θ±0.2°) of 16.0 and 19.2. In some embodiments, the Form C is characterized by an X-Ray powder diffraction pattern comprising at least characteristic peaks at a diffraction angle (2Θ±0.2°) of 3.9 and 19.2. In some embodiments, the Form C is characterized by an X-Ray powder diffraction pattern comprising at least characteristic peaks at a diffraction angle (2Θ±0.2°) of 3.9, 16.0, and 19.2. In some embodiments, the Form C is characterized by an X-Ray powder diffraction pattern comprising at least characteristic peaks at a diffraction angle (2Θ±0.2°) of 3.9, 7.6, 16.0, and 19.2. In some embodiments, the Form C is characterized by an X-Ray powder diffraction pattern comprising at least characteristic peaks at a diffraction angle (2Θ±0.2°) of 3.9, 7.6, 16.0, 18.4 and 19.2. In some embodiments, the Form C is characterized by an X-Ray powder diffraction pattern comprising at least characteristic peaks at a diffraction angle (2Θ±0.2°) of 7.6, 16.0, 18.0, 19.2, and 28.4. In some embodiments, the Form C is characterized by an X-Ray powder diffraction pattern comprising at least characteristic peaks at a diffraction angle (2Θ±0.2°) of 7.6, 16.0, 18.0, 19.2, 26.7, and 28.4. For example, in some embodiments, the Form C is characterized by an X-Ray powder diffraction pattern comprising at least characteristic peaks at a diffraction angle (2Θ±0.2°) of 3.9, 7.6, 16.0, 18.0, 19.2, 26.7, 27.0, and 28.4.

In certain embodiments, the Form C is characterized by an X-Ray powder diffraction pattern, obtained with Ni-filtered Cu Kα (45 kV/40 mA) radiation, comprising at least two or three d-spacing values (d-spacing±0.2 Å) selected from 22.9, 5.6, 5.0, 4.8, 4.6, 3.3, and 3.2.

In some embodiments, the Form C is characterized by an X-Ray powder diffraction pattern comprising at least d-spacing values (d-spacing±0.2 Å) at 5.6 and 4.6. In some embodiments, the Form C is characterized by an X-Ray powder diffraction pattern comprising at least d-spacing values (d-spacing±0.2 Å) at 22.9 and 4.6. In some embodiments, the Form C is characterized by an X-Ray powder diffraction pattern comprising at least d-spacing values (d-spacing±0.2 Å) at 22.9, 5.6, and 4.6. In some embodiments, the Form C is characterized by an X-Ray powder diffraction pattern comprising at least d-spacing values (d-spacing±0.2 Å) at 22.9, 5.6, 4.6, and 3.2. In some embodiments, the Form C is characterized by an X-Ray powder diffraction pattern comprising at least d-spacing values (d-spacing±0.2 Å) at 5.3, 4.8, 4.6, and 3.2. In some embodiments, the Form C is characterized by an X-Ray powder diffraction pattern comprising at least d-spacing values (d-spacing±0.2 Å) at 22.9, 5.3, 4.8, 4.6, and 3.2. In some embodiments, the Form C is characterized by an X-Ray powder diffraction pattern comprising at least d-spacing values (d-spacing±0.2 Å) at 11.6, 5.3, 4.8, 4.6, and 3.2. For example, in some embodiments, the Form C is characterized by an X-Ray powder diffraction pattern comprising at least d-spacing values (d-spacing±0.2 Å) at 22.9, 5.6, 5.0, 4.8, 4.6, 3.3, and 3.2.

In some embodiments, the Form C is characterized by a differential scanning calorimetry (DSC) thermogram with an endothermic event ranging in temperature of from about 50° C. to about 125° C. with a peak temperature of about 105° C. In some embodiments, additional endothermic events ranging from about 225 to about 255° C. are observed with peak temperature of about 242° C. and about 255° C. In some embodiments, the endotherms are observed when using a scan rate of 15° C./min.

In some embodiments, the Form C is characterized by a thermogravimetric analysis (TGA-IR) thermogram with about a 3.2% stepwise weight loss event of water ranging in temperature of from about 25 to about 175° C. In some embodiments, the stepwise weight loss event of water corresponds to dehydration of the monohydrate salt. In some embodiments, the Form C can be heated up to 255° C. with no observed degradation confirmed by FTIR after cooling. In some embodiments, the stepwise weight loss of water is observed when using a scan rate of 15° C./min.

Form D

Another crystalline form of Formula (I) is known as Form D. In some embodiments, Form D is a non-solvated crystalline form of Formula (I). In some embodiments, Form D is an anhydrous crystalline form of Formula (I).

In certain embodiments, the Form D is characterized by an X-Ray powder diffraction pattern, obtained with Ni-filtered Cu Kα (45 kV/40 mA) radiation, comprising at least two or three peaks at diffraction angles (2Θ±0.2°) selected from 7.1, 13.9, 15.5, 17.2, 19.6, 19.9, 20.8, and 27.9. For example, see FIG. 5A.

In some embodiments, the Form D is characterized by an X-Ray powder diffraction pattern comprising at least characteristic peaks at a diffraction angle (2Θ±0.2°) of 7.1 and 20.8. In some embodiments, the Form D is characterized by an X-Ray powder diffraction pattern comprising at least characteristic peaks at a diffraction angle (2Θ±0.2°) of 7.1 and 19.6. In some embodiments, the Form D is characterized by an X-Ray powder diffraction pattern comprising at least characteristic peaks at a diffraction angle (2Θ±0.2°) of 7.1, 19.6, and 20.8. In some embodiments, the Form D is characterized by an X-Ray powder diffraction pattern comprising at least characteristic peaks at a diffraction angle (2Θ±0.2°) of 7.1, 17.2, 19.6, and 20.8. In some embodiments, the Form D is characterized by an X-Ray powder diffraction pattern comprising at least characteristic peaks at a diffraction angle (2Θ±0.2°) of 7.1, 15.5, 17.2, 19.6, and 20.8. In some embodiments, the Form D is characterized by an X-Ray powder diffraction pattern comprising at least characteristic peaks at a diffraction angle (2Θ±0.2°) of 7.1, 15.5, 17.2, 19.6, 20.8, and 27.9. In some embodiments, the Form D is characterized by an X-Ray powder diffraction pattern comprising at least characteristic peaks at a diffraction angle (2Θ±0.2°) of 7.1, 17.2, 19.6, 20.8, and 27.9. For example, in some embodiments, the Form D is characterized by an X-Ray powder diffraction pattern comprising at least characteristic peaks at a diffraction angle (2Θ±0.2°) of 7.1, 13.9, 15.5, 17.2, 19.6, 19.9, 20.8, and 27.9.

In certain embodiments, the Form D is characterized by an X-Ray powder diffraction pattern, obtained with Ni-filtered Cu Kα (45 kV/40 mA) radiation, comprising at least two or three d-spacing values (d-spacing±0.2 Å) selected from 12.5, 6.4, 5.7, 5.2, 4.5, 4.4, 4.3, and 3.2.

In some embodiments, the Form D is characterized by an X-Ray powder diffraction pattern comprising at least d-spacing values (d-spacing±0.2 Å) at 12.5 and 4.3. In some embodiments, the Form D is characterized by an X-Ray powder diffraction pattern comprising at least d-spacing values (d-spacing±0.2 Å) at 12.5 and 4.5. In some embodiments, the Form D is characterized by an X-Ray powder diffraction pattern comprising at least d-spacing values (d-spacing±0.2 Å) at 12.5, 4.5, and 4.3. In some embodiments, the Form D is characterized by an X-Ray powder diffraction pattern comprising at least d-spacing values (d-spacing±0.2 Å) at 12.5, 5.2, 4.5, and 4.3. In some embodiments, the Form D is characterized by an X-Ray powder diffraction pattern comprising at least d-spacing values (d-spacing±0.2 Å) at 12.5, 6.4, 5.2, 4.5, and 4.3. In some embodiments, the Form D is characterized by an X-Ray powder diffraction pattern comprising at least d-spacing values (d-spacing±0.2 Å) at 12.5, 5.2, 4.5, 4.3, and 3.2. For example, in some embodiments, the Form D is characterized by an X-Ray powder diffraction pattern comprising at least d-spacing values (d-spacing±0.2 Å) at 12.5, 6.4, 5.7, 5.2, 4.5, 4.4, 4.3, and 3.2.

In some embodiments, the Form D is characterized by a differential scanning calorimetry (DSC) thermogram with an endothermic event ranging in temperature of from about 245° C. to about 280° C. with a peak temperature of about 266° C. In some embodiments, the endothermic event occurs with decomposition. In some embodiments, the endotherms are observed when using a scan rate of 15° C./min.

In some embodiments, the Form D is characterized by a thermogravimetric analysis (TGA-IR) thermogram with about a 0.6% weight loss event ranging in temperature of from about 25° C. to about 150° C. In some embodiments, the weight loss event is observed when using a scan rate of 15° C./min.

Form E

Another crystalline form of Formula (I) is known as Form E. Form E is a monohydrate crystalline form.

In certain embodiments, the Form E is characterized by an X-Ray powder diffraction pattern, obtained with Ni-filtered Cu Kα (45 kV/40 mA) radiation, comprising at least two or three peaks at diffraction angles (2Θ±0.2°) selected from 10.1, 12.5, 14.8, 16.3, 16.6, 18.7, 22.0, 23.4, and 26.2. For example, see FIG. 7A.

In some embodiments, the Form E is characterized by an X-Ray powder diffraction pattern comprising at least characteristic peaks at a diffraction angle (2Θ±0.2°) of 10.1 and 16.3. In some embodiments, the Form E is characterized by an X-Ray powder diffraction pattern comprising at least characteristic peaks at a diffraction angle (2Θ±0.2°) of 16.3 and 18.7. In some embodiments, the Form E is characterized by an X-Ray powder diffraction pattern comprising at least characteristic peaks at a diffraction angle (2Θ±0.2°) of 16.3 and 22.0. In some embodiments, the Form E is characterized by an X-Ray powder diffraction pattern comprising at least characteristic peaks at a diffraction angle (2Θ±0.2°) of 10.1, 16.3, and 18.7. In some embodiments, the Form E is characterized by an X-Ray powder diffraction pattern comprising at least characteristic peaks at a diffraction angle (2Θ±0.2°) of 10.1, 16.3, and 22.0. In some embodiments, the Form E is characterized by an X-Ray powder diffraction pattern comprising at least characteristic peaks at a diffraction angle (2Θ±0.2°) of 10.1, 16.3, 18.7, and 22.0. In some embodiments, the Form E is characterized by an X-Ray powder diffraction pattern comprising at least characteristic peaks at a diffraction angle (2Θ±0.2°) of 10.1, 14.8, 16.3, 18.7, and 22.0. For example, in some embodiments, the Form E is characterized by an X-Ray powder diffraction pattern comprising at least characteristic peaks at a diffraction angle (2Θ±0.2°) of 10.1, 12.5, 14.8, 16.3, 16.6, 18.7, 22.0, 23.4, and 26.2.

In certain embodiments, the Form E is characterized by an X-Ray powder diffraction pattern, obtained with Ni-filtered Cu Kα (45 kV/40 mA) radiation, comprising at least two or three d-spacing values (d-spacing±0.2 Å) selected from 8.8, 7.1, 6.0, 5.5, 5.4, 4.8, 4.6, 4.1.

In some embodiments, the Form E is characterized by an X-Ray powder diffraction pattern comprising at least d-spacing values (d-spacing±0.2 Å) at 8.8 and 5.5. In some embodiments, the Form E is characterized by an X-Ray powder diffraction pattern comprising at least d-spacing values (d-spacing±0.2 Å) at 5.5 and 4.1. In some embodiments, the Form E is characterized by an X-Ray powder diffraction pattern comprising at least d-spacing values (d-spacing±0.2 Å) at 5.5 and 4.8. In some embodiments, the Form E is characterized by an X-Ray powder diffraction pattern comprising at least d-spacing values (d-spacing±0.2 Å) at 8.8, 5.5, and 4.1. In some embodiments, the Form E is characterized by an X-Ray powder diffraction pattern comprising at least d-spacing values (d-spacing±0.2 Å) at 8.8, 5.5, and 4.8. In some embodiments, the Form E is characterized by an X-Ray powder diffraction pattern comprising at least d-spacing values (d-spacing±0.2 Å) at 8.8, 5.5, 4.8, and 4.1. For example, in some embodiments, the Form E is characterized by an X-Ray powder diffraction pattern comprising at least d-spacing values (d-spacing±0.2 Å) at 8.8, 7.1, 6.0, 5.5, 5.4, 4.8, 4.6, and 4.1.

In some embodiments, the Form E is characterized by a differential scanning calorimetry (DSC) thermogram with an endothermic event ranging from a temperature of about 85° C. to about 150° C. with a peak temperature of about 136° C. In some embodiments, an additional endothermic event ranging from a temperature of about 200 to about 225° C. is observed with peak temperature of about 221° C. In some embodiments, the additional endothermic event occurs with decomposition. In some embodiments, the endotherms are observed when using a scan rate of 15° C./min.

In some embodiments, the Form E is characterized by a thermogravimetric analysis (TGA-IR) thermogram with about a 3.1% stepwise weight loss event of water ranging from a temperature of about 85° C. to about 150° C. In some embodiments, the stepwise weight loss of water corresponds to dehydration of the monohydrate salt. In some embodiments, an additional step-wise weight loss event of about 7.1% carbon dioxide is observed ranging from a temperature from about 175° C. to about 210° C. In some embodiments, the addition weight loss of event of carbon dioxide occurs with decomposition. In some embodiments, the weight loss events are observed when using a scan rate of 15° C./min.

In some embodiments, the experimental powder diffraction patterns are obtained by diffraction of X-rays on powder in a PANalytical X'Pert Pro diffractometer using Ni-filtered Cu Kα (45 kV/40 mA) radiation and a step size of 0.02° 2θ and X'celerator™ RTMS (Real Time Multi-Strip) detector. In some embodiments, the samples, without grinding, are put on a glass plate and are analyzed at ambient temperature and humidity. In some embodiments, configuration on the incidental beam side comprises a fixed divergence slit (0.25°), 0.04 rad Soller slits, anti-scatter slit (0.25°), and 10 mm beam mask. In some embodiments, configuration on the diffracted beam side comprises a fixed divergence slit (0.25°) and 0.04 rad Soller slit. In some examples, the peaks with a relative intensity of more than about 10% are considered as characteristic peaks.

One skilled in the art will understand that the relative intensities and positions of the peaks obtained by X-Ray powder diffraction may vary depending upon factors such as, the sample preparation technique, the sample mounting procedure and the particular instrument employed. For example, in additional embodiments, the listed X-Ray powder diffraction pattern peaks for the crystalline form of Formula (I) may be ±0.2 degrees 2Θ and the d-spacing ±0.2 Å.

It is known that an X-ray powder diffraction pattern may be obtained which has one or more measurement errors depending on measurement conditions (such as equipment used). Intensities in an X-ray powder diffraction pattern may fluctuate depending on measurement conditions. Therefore, it should be understood that the crystalline forms of the present invention are not limited to the crystals that provide X-ray powder diffraction patterns identical to the X-ray powder diffraction patterns described in this application, and any crystals providing X-ray powder diffraction patterns substantially the same (e.g., 2Θ±0.2°) as those described in the application fall within the scope of the present invention. For example, relative intensity of peaks can be affected by grains above 30 microns in size and non-unitary aspect ratios, which may affect analysis of samples. A person skilled in the art will recognize that the position of reflections can be affected by the precise height at which the sample sits in the diffractometer and the zero calibration of the diffractometer. The surface planarity of the sample may also have a small effect. Therefore, the diffraction pattern data described herein are not to be taken as absolute values. (See, e.g., Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

In some embodiments, the crystalline compound of Formula (I) comprises at least about 50% Form A, at least about 60% Form A, at least about 70% Form A, or at least about 80% Form A by wt., in relation to the total amount of crystalline forms present in the crystalline compound of Formula (I). In some embodiments, the crystalline Form A of Formula (I) is isolated in a substantially pure crystalline form (e.g., substantially free of one or more other crystalline forms of Formula (I)). In some embodiments, the crystalline compound of Formula (I) comprises at least about 90% Form A, at least about 91% Form A, at least about 92% Form A, at least about 93% Form A, at least about 94% Form A, at least about 95% Form A, at least about 96% Form A, at least about 97% Form A, at least about 98% Form A, at least about 99% Form A, or about 100% Form A in relation to the total amount of crystalline forms present in the compound of Formula (I). In some embodiments, the crystalline compound of Formula (I) comprises from about 80%, about 85%, or about 90% Form A, to about 95%, about 96%, about 97%, about 98%, about 99%, or about 99.9% Form A, such as for example, from about 80% Form A to about 99.9% Form A, from about 85% Form A to about 99% Form A, from about 90% Form A to about 99% Form A, or from about 90% Form A to about 95% Form A in relation to the total amount of crystalline forms present in the compound of Formula (I). In some embodiments, the compound of Formula (I) is predominantly crystalline Form A with no more than about 10%, about 9%, about 8%, about 7%, about 6%, about 5%, about 4%, about 3%, about 2%, or about 1% of other crystalline forms of Formula (I), e.g., Form B, C, D, and E. The crystalline purity of Form A of Formula (I) may be determined by XRPD. In some embodiments, the crystalline purity of Form A may be limited by the detection limits of the diffractometer such that the crystalline purity of Form A may not be greater than about 95%, greater than about 96%, greater than about 97%, greater than about 98%, or greater than about 99% in relation to the total amount of crystalline forms present in the compound of Formula (I).

In some embodiments, the crystalline compound of Formula (I) comprises at least about 50% Form B, at least about 60% Form B, at least about 70% Form B, or at least about 80% Form B by wt., in relation to the total amount of crystalline forms present in the compound of Formula (I). In some embodiments, the Form B of Formula (I) is isolated in a substantially pure crystalline form (e.g., substantially free of one or more other crystalline forms of Formula (I)). In some embodiments, the crystalline compound of Formula (I) comprises at least about 90% Form B, at least about 91% Form B, at least about 92% Form B, at least about 93% Form B, at least about 94% Form B, at least about 95% Form B, at least about 96% Form B, at least about 97% Form B, at least about 98% Form B, at least about 99% Form B, or about 100% Form B in relation to the total amount of crystalline forms present in the compound of Formula (I). In some embodiments, the crystalline compound of Formula (I) comprises from about 80%, about 85%, or about 90% Form B, to about 95%, about 96%, about 97%, about 98%, about 99%, or about 99.9% Form B, such as for example, from about 80% Form B to about 99.9% Form B, from about 85% Form B to about 99% Form B, from about 90% Form B to about 99% Form B, or from about 90% Form B to about 95% Form B in relation to the total amount of crystalline forms present in the compound of Formula (I). In some embodiments, the compound of Formula (I) is predominantly crystalline Form B with no more than about 10%, about 9%, about 8%, about 7%, about 6%, about 5%, about 4%, about 3%, about 2%, or about 1% of other crystalline forms of Formula (I), e.g., Form A, C, D, and E. The crystalline purity of Form B of Formula (I) may be determined by XRPD. In some embodiments, the crystalline purity of Form B may be limited by the detection limits of the diffractometer such that the crystalline purity of Form B may not be greater than about 95%, greater than about 96%, greater than about 97%, greater than about 98%, or greater than 99% in relation to the total amount of crystalline forms present in the compound of Formula (I).

In some embodiments, the crystalline compound of Formula (I) comprises at least about 50% Form C, at least about 60% Form C, at least about 70% Form C, or at least about 80% Form C by wt., in relation to the total amount of crystalline forms present in the crystalline compound of Formula (I). In some embodiments, the Form C of Formula (I) is isolated in a substantially pure crystalline form (e.g., substantially free of one or more other crystalline forms of Formula (I)). In some embodiments, the crystalline compound of Formula (I) comprises at least about 90% Form C, at least about 91% Form C, at least about 92% Form C, at least about 93% Form C, at least about 94% Form C, at least about 95% Form C, at least about 96% Form C, at least about 97% Form C, at least about 98% Form C, at least about 99% Form C, or about 100% Form A in relation to the total amount of crystalline forms present in the compound of Formula (I). In some embodiments, the crystalline compound of Formula (I) comprises from about 80%, about 85%, or about 90% Form C, to about 95%, about 96%, about 97%, about 98%, about 99%, or about 99.9% Form C, such as for example, from about 80% Form C to about 99.9% Form C, from about 85% Form C to about 99% Form C, from about 90% Form C to about 99% Form C, or from about 90% Form C to about 95% Form C in relation to the total amount of crystalline forms present in the compound of Formula (I). In some embodiments, the compound of Formula (I) is predominantly crystalline Form C with no more than about 10%, about 9%, about 8%, about 7%, about 6%, about 5%, about 4%, about 3%, about 2%, or about 1% of other crystalline forms of Formula (I), e.g., Form A, B, D, and E. The crystalline purity of Form C of Formula (I) may be determined by XRPD. In some embodiments, the crystalline purity of Form C may be limited by the detection limits of the diffractometer such that the crystalline purity of Form C may not be greater than about 95%, greater than about 96%, greater than about 97%, greater than about 98%, or greater than about 99% in relation to the total amount of crystalline forms present in the compound of Formula (I).

In some embodiments, the crystalline compound of Formula (I) comprises at least about 50% Form D, at least about 60% Form D, at least about 70% Form D, or at least about 80% Form D by wt., in relation to the total amount of crystalline forms present in the crystalline compound of Formula (I). In some embodiments, the Form D of Formula (I) is isolated in a substantially pure crystalline form (e.g., substantially free of one or more other crystalline forms of Formula (I)). In some embodiments, the crystalline compound of Formula (I) comprises at least about 90% Form D, at least about 91% Form D, at least about 92% Form D, at least about 93% Form D, at least about 94% Form D, at least about 95% Form D, at least about 96% Form D, at least about 97% Form D, at least about 98% Form D, at least about 99% Form D, or about 100% Form D in relation to the total amount of crystalline forms present in the compound of Formula (I). In some embodiments, the crystalline compound of Formula (I) comprises from about 80%, about 85%, or about 90% Form D, to about 95%, about 96%, about 97%, about 98%, about 99%, or about 99.9% Form D, such as for example, from about 80% Form D to about 99.9% Form D, from about 85% Form D to about 99% Form D, from about 90% Form D to about 99% Form D, or from about 90% Form D to about 95% Form D in relation to the total amount of crystalline forms present in the compound of Formula (I). In some embodiments, the compound of Formula (I) is predominantly crystalline Form D with no more than about 10%, about 9%, about 8%, about 7%, about 6%, about 5%, about 4%, about 3%, about 2%, or about 1% of other crystalline forms of Formula (I), e.g., Form A, B, C, and E. The crystalline purity of Form D of Formula (I) may be determined by XRPD. In some embodiments, the crystalline purity of Form D may be limited by the detection limits of the diffractometer such that the crystalline purity of Form D may not be greater than about 95%, greater than about 96%, greater than about 97%, greater than about 98%, or greater than about 99% in relation to the total amount of crystalline forms present in the compound of Formula (I).

In some embodiments, the crystalline compound of Formula (I) comprises at least about 50% Form E, at least about 60% Form E, at least about 70% Form E, or at least about 80% Form E by wt., in relation to the total amount of crystalline forms present in the crystalline compound of Formula (I). In some embodiments, the Form E of Formula (I) is isolated in a substantially pure crystalline form (e.g., substantially free of one or more other crystalline forms of Formula (I)). In some embodiments, the crystalline compound of Formula (I) comprises at least about 90% Form E, at least about 91% Form E, at least about 92% Form E, at least about 93% Form E, at least about 94% Form E, at least about 95% Form E, at least about 96% Form E, at least about 97% Form E, at least about 98% Form E, at least about 99%

Form E, or about 100% Form E in relation to the total amount of crystalline forms present in the compound of Formula (I). In some embodiments, the crystalline compound of Formula (I) comprises from about 80%, about 85%, or about 90% Form E, to about 95%, about 96%, about 97%, about 98%, about 99%, or about 99.9% Form E, such as for example, from about 80% Form E to about 99.9% Form E, from about 85% Form E to about 99% Form E, from about 90% Form E to about 99% Form E, or from about 90% Form E to about 95% Form E in relation to the total amount of crystalline forms present in the compound of Formula (I). In some embodiments, the compound of Formula (I) is predominantly crystalline Form E with no more than about 10%, about 9%, about 8%, about 7%, about 6%, about 5%, about 4%, about 3%, about 2%, or about 1% of other crystalline forms of Formula (I), e.g., Form A, B, C, and D. The crystalline purity of Form E of Formula (I) may be determined by XRPD. In some embodiments, the crystalline purity of Form E may be limited by the detection limits of the diffractometer such that the crystalline purity of Form E may not be greater than about 95%, greater than about 96%, greater than about 97%, greater than about 98%, or greater than about 99% in relation to the total amount of crystalline forms present in the compound of Formula (I).

In some embodiments, Forms A-E of Formula (I) are crystalline solids. In other embodiments, Forms A-E of Formula (I) are crystalline solids substantially free of amorphous Formula (I). In an embodiment, the presence of amorphous Formula (I) may be determined by XRPD.

In certain embodiments, substantially pure crystalline forms of Formula (I) (e.g., Form A-E) can be obtained by various crystallization or recrystallization methods. In some embodiments, substantially pure crystalline forms of Formula (I) can be crystalized or recrystallized from solvents, including, but not limited to water, MeOH, 2-methoxyethanol, 1-propanol, nitromethane:DMSO (80:20), MeCN, DMSO, acetone, 2-butanone, DCM, methyl acetate, 4-methyl-2-pentanone, chloroform, EtOAc, chlorobenzene:DMSO (80:20), THF, 1,4-dioxane, isopropyl ether, toluene:DMSO (80:20), cyclohexane, heptane, 1-butanol, IPA, trifluoroethanol, dimethyl carbonate, MTBE, isopropyl acetate, ethanol, 1-methoxy-2-propanol, cyclohexanone, DMF, 2-methoxyethyl ether, MeOH:water (95:5), MeCN:water (95:5), acetone:water (95:5), THF:water (95:5), IPA:water (95:5), MeOH:water (90:10), MeCN:water (90:10), acetone:water (90:10), 1,4-dioxane:water (90:10), 2-propanol:water (90:10), acetone:water (80:20), THF:water (90:10), ethanol:water (20:80), 2-propanol:DMSO (80:20), MeCN:DMSO (80:20), and the like. In some embodiments, the recrystallization solvents can have a water activity ranging from 0.1 to 1.

In certain embodiments, the crystalline forms provided herein are subjected to milling conditions to comprise a particle size. The nomenclature describing the particle size of Formula (I) is commonly referred to, and is herein, as the "$D_{90}$." For example, a $D_{90}$ of 8 (or $D_{90}$=8) means that at least 90% (determined in relation to the total mass, total volume, and/or total number of particles) of the particles have a particle size of less than 8 microns. In some embodiments, the particle size distribution is determined by laser diffraction dry particle size analyzer resulting in a determination of the particle size distribution in relation to the total volume, i.e., $D_{90}$ of 8 (or $D_{90}$=8) means that at least 90% by volume (or vol.-%) of the particles have a particle size of less than 8 microns. In some embodiments, the crystalline forms provided herein comprise a particle size ($D_{90}$) of from about 1 μm to about 20 μm, such as from about 2, 3, 4, or 5 μm to about 15, 16, 17, 18, or 19 μm. In some embodiments, the crystalline forms provided herein comprise a particle size ($D_{90}$) of about 10, 11, 12, 13, 14, or 15 μm. In some embodiments, the crystalline forms provided herein comprise a particle size ($D_{90}$) of about 5, 6, 7, or 8 μm. In some embodiments, the crystalline forms provided herein comprise a particle size ($D_{90}$) of about 15 μm. In some embodiments, the crystalline forms provided herein comprise a particle size ($D_{90}$) of about 8 μm.

4.1.3. Therapeutic/Prophylactic Administration and Compositions of the Disclosure The crystalline forms of Formula (I) provided herein are advantageously useful in medicine. As described above, the crystalline forms of Formula (I) are useful for treating or preventing an Insomnia Disorder in a subject, e.g., a human, in need thereof. In another embodiment, the crystalline forms of Formula (I) are useful for treating an Insomnia Disorder in a subject, e.g., a human, in need thereof. In another embodiment, the crystalline forms of Formula (I) are useful for preventing an Insomnia Disorder in a subject, e.g., a human, in need thereof. In another embodiment, the crystalline forms of Formula (I) of the disclosure can be administered to any animal requiring modulation of the opioid and/or ORL-1 receptors. In another embodiment, a crystalline form of Formula (I) is useful for treating insomnia associated with alcohol cessation in a subject, e.g., a human, in need thereof. In certain embodiments, the useful crystalline form of Formula (I) is Form A.

When administered to a subject, e.g., a human, a crystalline form of Formula (I) can be administered as a component of a composition that comprises a pharmaceutically acceptable carrier or excipient.

Methods of administration include, but are not limited to, intradermal, intramuscular, intraperitoneal, parenteral, intravenous, subcutaneous, intranasal, epidural, oral, transmucosal, buccal, gingival, sublingual, intraocular, intracerebral, intravaginal, transdermal (e.g., via a patch), rectal, by inhalation, or topical, particularly to the ears, nose, eyes, or skin. In another embodiment, methods of administration include, but are not limited to, intravenous, oral, or by inhalation. The method of administration is left to the discretion of the practitioner. In some instances, administration will result in the release of a crystalline form of Formula (I) into the bloodstream. In other instances, administration will result in only local release of a crystalline form of Formula (I).

In yet another embodiment, a crystalline form of Formula (I) can be delivered in a controlled-release system or sustained-release system. Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a crystalline form of Formula (I) to treat or prevent the Insomnia Disorder or a symptom thereof in an extended amount of time. Advantages of controlled- or sustained-release compositions include extended activity of the drug, reduced dosing frequency, and increased compliance. In addition, controlled- or sustained-release compositions can favorably affect the time of onset of action or other characteristics, such as blood levels of the crystalline form of Formula (I), and can thus reduce the occurrence of adverse side effects.

Such dosage forms can be used to provide controlled- or sustained-release of one or more active ingredients using, for example, hydroxypropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

The compositions can optionally, but preferably, further comprise a suitable amount of a pharmaceutically acceptable excipient so as to provide the form for proper administration to a subject, e.g., a human. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a subject, e.g., a human. Water is a particularly useful excipient when a crystalline form of Formula (I) is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol mono-stearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, (Amer. Pharmaceutical Ass'n, Washington, DC, 1986), incorporated herein by reference. Other examples of suitable pharmaceutical excipients are described by Radebough et al., "Preformulation," pp. 1447-1676 in *Remington's Pharmaceutical Sciences* Vol. 2 (Gennaro, ed., $19^{th}$ Ed., Mack Publishing, Easton, PA, 1995), incorporated herein by reference.

The compositions can take the form of solutions, suspensions, emulsions, tablets such as an orally disintegrating tablet (ODT), a sublingual tablet, or a swallowed-intact tablet, pills, pellets, capsules, capsules containing liquids, powders, sustained-release formulations, suppositories, emulsions, aerosols, sprays, suspensions, microparticles, multiparticulates, rapidly dissolving films or other forms for oral or mucosal administration, or any other form suitable for use. In one embodiment, the composition is in the form of an ODT (see, e.g., U.S. Pat. Nos. 7,749,533 and 9,241,910). In another embodiment, the composition is in the form of a sublingual tablet (see, e.g., U.S. Pat. Nos. 6,572,891 and 9,308,175). In another embodiment, the composition is in the form of a capsule (see, e.g., U.S. Pat. No. 5,698,155). In another embodiment, the composition is in a form suitable for buccal administration, e.g., as a tablet, lozenge, gel, patch, or film, formulated in a conventional manner (see, e.g., Pather et al., "Current status and the future of buccal drug delivery systems," *Expert Opin. Drug Deliv.* 5(5):531-542 (2008)). In another embodiment, the composition is in a form suitable for gingival administration, e.g., as a polymeric film comprising polyvinyl alcohol, chitosan, polycarbophil, hydroxypropylcellulose, or Eudragit S-100, as disclosed by Padula et al., "In Vitro Evaluation of Mucoadhesive Films for Gingival Administration of Lidocaine," *AAPS Pharm Sci Tech* 14(4):1279-1283 (2013). In another embodiment, the composition is in a form of a swallowed-intact oral dosage form. In another embodiment, the composition is in a form suitable for intraocular administration.

In one embodiment, the crystalline forms of Formula (I) are formulated in accordance with routine procedures as a composition adapted for oral administration to human beings. A crystalline form of Formula (I) to be orally delivered can be in the form of tablets, capsules, gelcaps, caplets, lozenges, aqueous or oily solutions, suspensions, granules, microparticles, multiparticulates, powders, emulsions, syrups, or elixirs, for example. The oral dosage form can be a swallowed-intact oral dosage form, such as a tablet, capsule, or gelcap. When a crystalline form of Formula (I) is incorporated into oral tablets, such tablets can be compressed, tablet triturates, enteric-coated, sugar-coated, film-coated, multiply compressed, or multiply layered. Techniques and compositions for making solid oral dosage forms are described in *Pharmaceutical Dosage Forms: Tablets* (Lieberman et al., eds., $2^{nd}$ Ed., Marcel Dekker, Inc., 1989 and 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., $16^{th}$ Ed., Mack Publishing, Easton, PA, 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., $2^{nd}$ Ed., Marcel Dekker, Inc., 1996 and 1998).

An orally administered crystalline form of Formula (I) can contain one or more agents, for example, sweetening agents such as fructose, aspartame, or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol mono-stearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

When a crystalline form of Formula (I) is to be injected parenterally, it can be, e.g., in the form of an isotonic sterile solution. Alternatively, when a crystalline form of Formula (I) is to be inhaled, it can be formulated into a dry aerosol or can be formulated into an aqueous or partially aqueous solution.

In another embodiment, the crystalline form of Formula (I) can be formulated for intravenous administration. In certain embodiments, compositions for intravenous administration comprise sterile isotonic aqueous buffer. Where necessary, the compositions can also include a solubilizing agent. A crystalline form of Formula (I) for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a crystalline form of Formula (I) is to be administered by infusion, it can be dispensed, for example, with an infusion bottle containing sterile pharmaceutical grade water or saline. Where a crystalline form of Formula (I) is administered by injection, an ampule of sterile water for injection or saline can be provided so that the ingredients can be mixed prior to administration.

The amount of the crystalline form of Formula (I) that is effective for the treatment or prevention of an Insomnia Disorder can be determined by standard clinical techniques. In addition, in vitro and/or in vivo assays can optionally be employed to help identify optimal dose ranges. The precise dose to be employed will also depend on, e.g., the route of administration and the seriousness of the Insomnia Disorder, and can be decided according to the judgment of a practitioner and/or each animal's circumstances. In other examples thereof, variations will necessarily occur depending upon the weight and physical condition (e.g., hepatic and renal function) of the animal being treated, the disorder to be treated, the severity of the symptoms, the frequency of the dosing interval, the presence of any deleterious side-effects, and the particular compound utilized, among other things.

Effective dosage amounts of the disclosed crystalline forms of Formula (I) when used for the indicated effects, range from about 0.1 mg to about 5000 mg of the disclosed crystalline forms as needed for treatment, prevention or management of certain disorders. For example, pharmaceutical compositions for in vivo or in vitro use can contain about 0.1, 0.5, 5, 20, 50, 75, 100, 150, 250, 500, 750, 1000, 1250, 2500, 3500, or 5000 mg of the disclosed crystalline forms, or, in a range of from one amount to another amount in the list of doses. In one embodiment, a suitable effective dose of the crystalline form of Formula (I) administered to a human as a daily dose is from about 0.16 mg to about 8.0 mg. In one embodiment, a suitable effective daily dose of the crystalline form of Formula (I) administered to a human is about 0.16 mg. In other embodiments, a suitable effective daily dose of the crystalline form of Formula (I) administered to a human is about 0.20 mg, about 0.30 mg, about 0.33 mg, about 0.35 mg, about 0.40 mg, about 0.45 mg, about 0.46 mg, about 0.47 mg, about 0.48 mg, about 0.49 mg, about 0.50 mg, about 0.525 mg, about 0.55 mg, about 0.575 mg, about 0.60 mg, about 0.625 mg, about 0.65 mg, about 0.675 mg, about 0.70 mg, about 0.725 mg, about 0.75 mg, about 0.775 mg, about 0.80 mg, about 0.825 mg, about 0.85 mg, about 0.875 mg, about 0.90 mg, about 0.925 mg, about 0.95 mg, about 0.975 mg, about 1.00 mg, about 1.10 mg, about 1.20 mg, about 1.30 mg, about 1.40 mg, about 1.50 mg, about 1.60 mg, about 1.70 mg, about 1.80 mg, about 1.90 mg, about 2.00 mg, about 2.10 mg, about 2.20 mg, about 2.30 mg, about 2.40 mg, about 2.50 mg, about 2.60 mg, about 2.70 mg, about 2.80 mg, about 2.90 mg, about 3.00 mg, about 3.25 mg, about 3.50 mg, about 3.75 mg, about 4.0 mg, about 4.5 mg, about 5.0 mg, about 5.5 mg, about 6.0 mg, about 6.5 mg, about 7.0 mg, about 7.5 mg, or about 8.0 mg. In any of these embodiments, the daily dose is optionally a single daily dose. In any of these embodiments, the daily dose is optionally a divided daily dose, e.g., 67%, 60% 50%, 40%, or 33% of any of the above doses is administered before the intended bedtime and the remaining 33%, 40%, 50%, 60%, or 67%, respectively, is administered later during the daily period, such as upon middle-of-the night awakening followed by failure to readily return to sleep.

It is to be understood that the term "daily" means a 24 hour cycle beginning at the time of administration of a crystalline form of Formula (I). For example, for an ordinary overnight sleep cycle, if a crystalline form of Formula (I) is administered at 9:30 PM, then that "day" ends at 9:29 PM on the following calendar day. In another example, for a shift-worker's sleep cycle if a crystalline form of Formula (I) is administered at 8:15 AM, then that "day" ends at 8:14 AM on the following calendar day.

As known to those in the art, for a human a daily dose (in mg) can be converted to a mg/kg/day dosage amount by dividing the mg dose by 60 kg, an art-recognized average mass of a human. For example, a daily human dose of 1.25 mg is so-converted to a dosage amount of about 0.021 mg/kg/day.

The effective dosing amounts described herein refer to total amounts administered; that is, if more than one crystalline form of Formula (I) is administered, the effective dosing amount corresponds to the total amount administered.

Administration can be as a single dose or as a divided dose. In one embodiment, an effective dose or dosage amount is administered only as needed (pro re nata) such as, for example, in the event that sleep cannot readily be achieved, or upon middle-of-the night awakening followed by failure to readily return to sleep. In another embodiment, an effective dose or dosage amount is administered about every 24 hours, for example, before the intended bedtime, until the Insomnia Disorder is abated. In another embodiment, an effective dose or dosage amount is administered before the intended bedtime to abate the Insomnia Disorder. In other embodiments, an effective dose or dosage amount is administered before the intended bedtime on 2, 3, 4, 5, 6, 7, 8, 9, 10, up to 12, 12, at least 12, up to 14, 14, at least 14, up to 21, 21, at least 21, up to 28, 28, at least 28, up to 34, 34 at least 34, up to 40, 40, at least 40, up to 50, 50, at least 50, up to 60, 60, at least 60, up to 75, 75, at least 75, up to 90, 90, at least 90, up to 120, 120, at least 120, up to 150, 150, at least 150, up to 180, 180, at least 180, up to 270, 270, at least 270, up to 360, 360, or on at least 360 consecutive days to abate the Insomnia Disorder. In other embodiments, an effective dose or dosage amount is administered before the intended bedtime daily for at least 1, 2, 3, 4, 5, 6, 7, 8, 9, 10, up to 12, 12, at least 12, up to 16, 16, at least 16, up to 26, 26, at least 26, up to 52, 52, at least 52 weeks. In other embodiments, an effective dose or dosage amount is administered before the intended bedtime daily for at least 1, 2, 3, 4, 5, 6, 7, 8, 9, 10, up to 12, 12, at least 12 months. In any of these embodiments, the daily dose is optionally a single daily dose.

In one embodiment, an effective dose or dosage amount is administered in preparation for sleep, which can be, e.g., about 90 minutes before the intended bedtime. In other embodiments, an effective dose or dosage amount is administered in preparation for sleep, which can be about 75 minutes before, about 60 minutes before, about 45 minutes before, about 30 minutes before, about 20 minutes before, about 20 minutes or less before, about 15 minutes before, about 15 minutes or less before, about 10 minutes before, about 10 minutes or less before, about 5 minutes before, about 5 minutes or less before, about 2 minutes before, about 2 minutes or less before, or about 1 minute before the intended bedtime, or at the intended bedtime.

In one embodiment, an effective dose or dosage amount is administered daily to treat or prevent insomnia associated with alcohol cessation. In another embodiment, an effective dose or dosage amount is administered before the intended bedtime to treat or prevent insomnia associated with alcohol cessation. In another embodiment, an effective dose or dosage amount is administered starting after alcohol consumption is ceased (e.g., after a subject, e.g., a human with alcohol use disorder begins abstaining from alcohol consumption). In another embodiment, an effective dose or dosage amount that is administered starting after alcohol consumption is ceased can continue to be administered after alcohol is consumed (e.g., a subject, e.g., a human, who has abstained from alcohol consumes alcohol). In another embodiment, an effective dose or dosage amount is administered before alcohol consumption is ceased (e.g., while a subject, e.g., a human, with alcohol use disorder continues to consume). In other embodiments, an effective dose or dosage amount is administered starting at least 1, 2, 3, 4, 5, 6, 7, 8, 9, 10, up to 12, 12, at least 12, up to 14, 14, at least 14, up to 21, 21, at least 21, up to 28, 28, at least 28, up to 34, 34 at least 34, up to 40, 40, at least 40, up to 50, 50, at least 50, up to 60, 60, at least 60, up to 75, 75, at least 75, up to 90, 90, at least 90, up to 120, 120, at least 120, up to 150, 150, at least 150, up to 180, 180, at least 180, up to 270, 270, at least 270, up to 360, 360, or at least 360 days after alcohol consumption ceases. In other embodiments, an effective dose or dosage amount is administered starting at least 1, 2, 3, 4, 5, 6, 7, 8, 9, 10, up to 12, 12, at least 12, up to 16, 16, at least 16, up to 26, 26, at least 26, up to 52, 52, at least 52 weeks after alcohol consumption ceases. In other embodiments, an effective dose or dosage amount is administered starting at least 1, 2, 3, 4, 5, 6, 7, 8, 9, 10, up to 12, 12, at least 12 months after alcohol consumption ceases. In any of these embodiments, the daily dose is optionally a single daily dose.

A crystalline form of Formula (I) can be administered to a subject, e.g., a human, who has ingested alcohol or a subject, e.g., a human, may ingest alcohol following administration of the compound. In an embodiment, the amount of ethanol ingested is about 0.05 g/kg to about 5.0 g/kg; about 0.05 g/kg to about 2.0 g/kg; about 0.05 g/kg to about 1.0 g/kg; about 0.05 g/kg to about 0.5 g/kg; about 0.05 g/kg to about 0.2 g/kg; about 0.2 g/kg to about 5.0 g/kg; about 0.2 g/kg to about 2.0 g/kg; about 0.2 g/kg to about 1.0 g/kg; about 0.2 g/kg to about 0.8 g/kg; about 0.2 g/kg to about 0.5 g/kg; about 0.5 g/kg to about 5.0 g/kg; about 0.5 g/kg to about 2.0 g/kg; about 0.5 g/kg to about 1.0 g/kg; or about 0.5 g/kg to about 0.8 g/kg.

In one embodiment, a composition comprising a crystalline form of Formula (I) in accordance with the disclosure is used as a medicament. In another embodiment, compositions comprising a crystalline form of Formula (I) are disclosed which can be used for preparing a medicament containing said compositions.

In another embodiment, a composition comprising a crystalline form of Formula (I) is useful as a medicament in the treatment or prevention of a sleep disorder. In another embodiment, a composition comprising a crystalline form of Formula (I) is useful as a medicament in the treatment or prevention of a sleep disorder where the sleep disorder is an Insomnia Disorder, a hypersomnia disorder, a circadian rhythm sleep-wake disorder, an alcohol-induced sleep disorder, or any combination thereof.

In another embodiment, a composition comprising a crystalline form of Formula (I) is useful as a medicament in the treatment of a sleep disorder. In another embodiment, a composition comprising a crystalline form of Formula (I) is useful as a medicament in the treatment of a sleep disorder where the sleep disorder is an Insomnia Disorder, a hypersomnia disorder, a circadian rhythm sleep-wake disorder, an alcohol-induced sleep disorder, or any combination thereof.

In another embodiment, a composition comprising a crystalline form of Formula (I) is useful as a medicament in the prevention of a sleep disorder. In another embodiment, a composition comprising a crystalline form of Formula (I) is useful as a medicament in the prevention of a sleep disorder where the sleep disorder is an Insomnia Disorder, a hypersomnia disorder, a circadian rhythm sleep-wake disorder, an alcohol-induced sleep disorder, or any combination thereof.

In another embodiment, a composition comprising a crystalline form of Formula (I) is useful as a medicament in the treatment or prevention of an Insomnia Disorder. In another embodiment, a composition comprising a crystalline form of Formula (I) is useful as a medicament in the treatment of an Insomnia Disorder. In another embodiment, a composition comprising crystalline form of Formula (I) is useful as a medicament in the prevention of an Insomnia Disorder.

In another embodiment, a composition comprising a crystalline form of Formula (I) is useful as a medicament in the treatment or prevention of an alcohol-induced sleep disorder. In another embodiment, a composition comprising a crystalline form of Formula (I) is useful as a medicament in the treatment of an alcohol-induced sleep disorder. In another embodiment, a composition comprising a crystalline form of Formula (I) is useful as a medicament in the prevention of an alcohol-induced sleep disorder.

A composition of the disclosure is prepared by a method comprising admixing a crystalline form of Formula (I) with a pharmaceutically acceptable carrier or excipient. Admixing can be accomplished using methods known for admixing a compound (or derivative) and a pharmaceutically acceptable carrier or excipient. In one embodiment, the crystalline form of Formula (I) is present in the composition in an effective amount.

In another aspect, the present disclosure is directed to a method for treating, preventing or managing a disorder comprising administering to an animal in need thereof an effective amount of a crystalline compound as disclosed herein, wherein the disorder is a sleep disorder.

In an embodiment of said aspect, the sleep disorder is selected from the group consisting of insomnia; an alcohol-induced sleep disorder; insomnia in alcohol use disorder; a sleep disturbance associated with alcohol cessation; hypersomnia; circadian rhythm sleep-wake disorder; or any combination thereof.

In another aspect, the present disclosure is directed to a use of a crystalline compound as disclosed herein in the manufacture of a medicament for the treatment, prevention or management of a sleep disorder.

In an embodiment of said aspect, the sleep disorder is selected from the group consisting of insomnia; an alcohol-induced sleep disorder; insomnia in alcohol use disorder; a sleep disturbance associated with alcohol cessation; hypersomnia; circadian rhythm sleep-wake disorder; or any combination thereof.

In another aspect, the present disclosure is directed to a crystalline compound as disclosed herein for use in the treatment, prevention or management of a sleep disorder.

In an embodiment of said aspect, the sleep disorder is selected from the group consisting of insomnia; an alcohol-induced sleep disorder; insomnia in alcohol use disorder; a sleep disturbance associated with alcohol cessation; hypersomnia; circadian rhythm sleep-wake disorder; or any combination thereof.

4.1.4. Methods of Preparing Crystalline Forms

Provided herein are methods to prepare crystalline forms of Formula (I).

In some embodiments, a process for producing a crystalline Formula (I) comprises subjecting a crude form Formula (I) to crystallization or recrystallization conditions. In some embodiments, crude Formula (I) can be first dissolved in a suitable solution solvent (e.g., formic acid) at a temperature (e.g., 25° C.). In some instances, the solution of dissolved Formula (I) can be then be filtered to remove solid particulate. In some embodiments, to the solution of dissolved Formula (I), is added a suitable antisolvent (e.g., EtOAc). An antisolvent can include a solvent in which Formula (I) is less soluble then in the solution solvent. The antisolvent can be added to the solution quickly or slowly over an amount of time that varies depending on the scale of the reaction at a temperature of from about 10° C. to about 60° C. In some embodiments, the antisolvent comprising solution is aged with agitation at a temperature of from about 10° C. to about 60° C. for a period of time (e.g., 1 to 48 hours) to form a slurry. In some embodiments, the aging solution forms a slurry. In some embodiments, the aging solution is seeded with a crystalline form of Formula (I) (e.g., Form A) to form a slurry. In certain embodiments, the slurry is further treated with p-toluenesulfonic acid (p-TsOH) in a suitable solvent (e.g., ethanol). The slurry can then be optionally cooled and filtered to form a filter cake. In some embodiments, the process can further comprise drying the filter cake under reduced pressure at a temperature (e.g., 50° C.), and for an amount of time of from about 2 h to about 24 h, or until a transferrable solid of a crystalline form of Formula (I) is achieved. In specific embodiments, the crystalline form of Formula (I) is Form A as determined by powder X-ray diffraction. In some instances, Form A is obtained in a substantially pure crystalline form. In some embodiments, the recrystallization process can be repeated to obtain Form A substantially pure crystalline form.

5. EXAMPLES

Instrumentation and Analytical Methods

FT-Raman Spectroscopy (FTIR). Raman spectra were collected with a Nicolet NXR9650 or NXR 960 spectrometer (Thermo Electron) equipped with 1064 nm Nd:YVO$_4$ excitation laser, InGaAs and liquid-N$_2$ cooled Ge detectors, and a MicroStage. All spectra were acquired at 4 cm$^{-1}$ resolution, 64 scans, using Happ-Genzel apodization function and 2-level zero-filling through a glass cover.

Polarized-Light Microscopy (PLM). The photomicrographs were collected using Olympus BX60 polarized-light microscope equipped with Olympus DP70 camera.

Powder X-Ray Diffraction (PXRD). PXRD diffractograms were acquired on:
(1) PANalytical X'Pert Pro diffractometer using Ni-filtered Cu Kα (45 kV/40 mA) radiation and a step size of 0.02° 2θ and X'celerator™ RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit; or
(2) Rigaku RINT TTR III diffractometer using Cu Kα (50 kV/300 mA) radiation Differential Scanning calorimetry (DSC). DSC was conducted with a TA Instruments Q100 differential scanning calorimeter equipped with an autosampler and a refrigerated cooling system under 40 mL/min N$_2$ purge. DSC thermograms were obtained in crimped Al pans at 15° C./min in Al pans, unless noted otherwise. The temperatures of transitions recorded by DSC analysis are reported as onset values.

Thermogravimetric Analysis (TGA). TGA thermograms were obtained with a TA Instruments Q500 thermogravimetric analyzer under 40 mL/min N$_2$ purge at 15° C./min in Al pans, unless noted otherwise.

Thermogravimetric Analysis with IR Off-Gas Detection (TGA-IR). TGA-IR was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min N$_2$ flow and heating rate of 15° C./min in Pt or Al pans, unless noted otherwise. IR spectra were collected at 4 $_{cm}$$^{-1}$ resolution and 32 scans at each time point.

Example 1: Synthesis of Formula (I)

Step 1

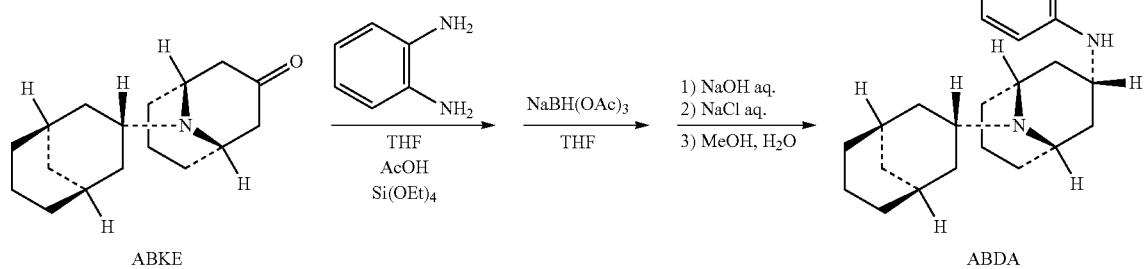

ABKE

ABDA

-continued

Step 2

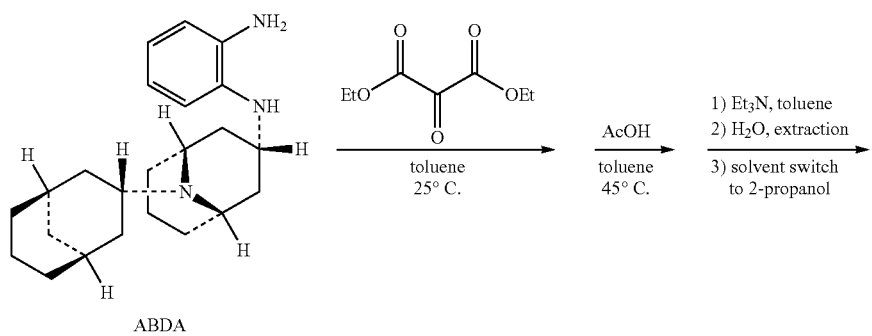

Step 3

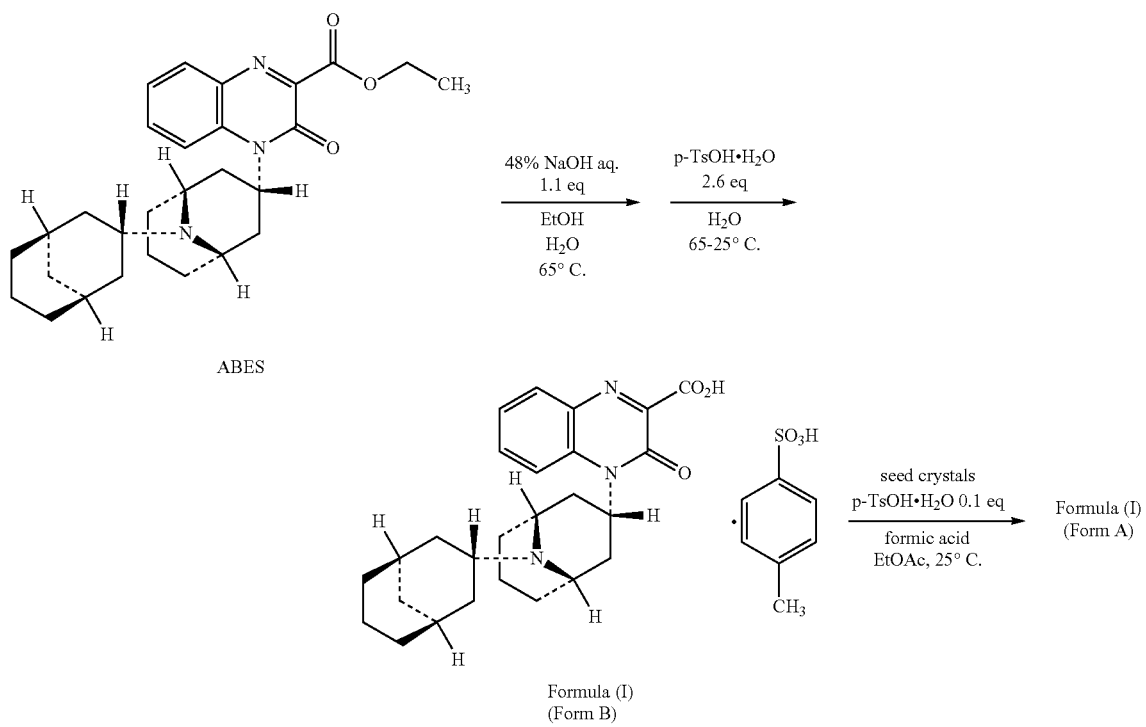

Step 1. A mixture of ABKE (15 kg), o-phenylenediamine, tetraethoxysilane, tetrahydrofuran, and acetic acid was stirred for a period of time and then mixed with NaBH(OAc)₃ in THF. When the reaction reached an acceptable conversion, the reaction mixture was poured into aqueous sodium hydroxide (NaOH). After phase separation, the organic layer was washed with aqueous NaOH and then aqueous sodium chloride. To the organic layer, methanol and water were added followed by ABDA seed crystals. After dropwise addition of water, the formed slurry was filtered and the filter cake was washed with cold methanol. The resulting cake was dried to provide ABDA (15.68 kg, 77.3%) as a solid. ABKE starting material may be prepared, for example, according to Example 1 in U.S. Pat. No. 8,476,271.

Step 2. A solution of ABDA (15.5 kg) and diethyl ketomalonate in toluene was mixed with hot acetic acid to form ABES. The reaction mixture was diluted with toluene and quenched with triethylamine. After washing the mixture with water and phase separation, the organic phase was concentrated under reduced pressure and 2-propanol was charged. Concentration and charge of 2-propanol were repeated for solvent exchange. The slurry was filtered and the filter cake was washed with 2-propanol. Drying gave ABES (18.48 kg, 90.9%) as a solid.

Step 3. Aqueous NaOH was added to a slurry of ABES (18 kg) in ethanol and purified water. The mixture was stirred with heating to form the corresponding intermediate sodium carboxylate salt. To the reaction mixture, a solution of p-toluenesulfonic acid (p-TsOH) in purified water was added to neutralize the intermediate sodium carboxylate salt and form Formula (I). The slurry was filtered and the filter cake of Formula (I) was washed with purified water. The identity of Formula (I) was confirmed using $^1$H NMR and LC/MS. The polymorphic form observed by PXRD was designated Form B. FIG. 1 shows the PXRD pattern of Formula (I) as Form B. The peaks of the X-ray powder diffraction pattern is shown in Table 1, below.

TABLE 1

PXRD peaks of Form B of Formula (I)

| 2-Theta | d-spacing [Å] | Height | H % |
|---|---|---|---|
| 6.840 | 12.9125 | 5,702 | 89 |
| 7.040 | 12.5461 | 6,453 | 100 |
| 11.160 | 7.9220 | 488 | 8 |
| 11.240 | 7.8657 | 561 | 9 |
| 11.320 | 7.8103 | 572 | 9 |
| 13.440 | 6.5827 | 399 | 7 |
| 13.480 | 6.5633 | 394 | 7 |
| 13.600 | 6.5057 | 387 | 6 |
| 13.760 | 6.4304 | 787 | 13 |
| 13.960 | 6.3387 | 707 | 11 |
| 14.880 | 5.9488 | 391 | 7 |
| 15.520 | 5.7049 | 627 | 10 |
| 15.580 | 5.6830 | 654 | 11 |
| 16.060 | 5.5143 | 436 | 7 |
| 16.220 | 5.4602 | 563 | 9 |
| 16.900 | 5.2420 | 445 | 7 |
| 17.160 | 5.1632 | 1,051 | 17 |
| 17.220 | 5.1453 | 1,244 | 20 |
| 18.220 | 4.8651 | 422 | 7 |
| 18.280 | 4.8493 | 433 | 7 |
| 18.560 | 4.7767 | 1,164 | 19 |
| 18.600 | 4.7666 | 1,162 | 18 |
| 19.480 | 4.5532 | 1,055 | 17 |
| 19.620 | 4.5210 | 2,083 | 33 |
| 19.940 | 4.4492 | 744 | 12 |
| 19.980 | 4.4403 | 596 | 10 |
| 20.740 | 4.2793 | 2,554 | 40 |
| 20.940 | 4.2389 | 1,883 | 30 |
| 21.320 | 4.1642 | 420 | 7 |
| 24.300 | 3.6598 | 606 | 10 |
| 24.460 | 3.6363 | 646 | 11 |
| 24.520 | 3.6275 | 564 | 9 |
| 25.360 | 3.5092 | 424 | 7 |
| 25.940 | 3.4321 | 444 | 7 |
| 26.020 | 3.4217 | 484 | 8 |
| 26.260 | 3.3910 | 524 | 9 |
| 27.800 | 3.2065 | 1,108 | 18 |
| 27.960 | 3.1885 | 1,097 | 17 |
| 29.840 | 2.9918 | 746 | 12 |
| 29.900 | 2.9859 | 756 | 12 |
| 29.960 | 2.9801 | 751 | 12 |
| 30.040 | 2.9723 | 441 | 7 |
| 30.860 | 2.8952 | 506 | 8 |
| 30.940 | 2.8879 | 546 | 9 |

The Formula (I) from step 3 was further dried and then dissolved in formic acid and polished by filter. To the solution, ethyl acetate and Formula (I) (Form A) seed crystals were added to increase the rate of crystallization and provide a slurry of Formula (I). Form (A) would crystallize slowly without the use of seed crystals. After aging, additional ethyl acetate and a small amount of p-TsOH were added. The slurry was filtered and the filter cake was washed with ethyl acetate. Drying gave purified Formula (I) as a crystalline solid. After milling, 21.14 kg of Formula (I) (API) was afforded in 89.6% yield from ABES. The identity of Formula (I) was confirmed using $^1$H NMR and LC/MS. The polymorphic form observed by PXRD was designated Form A. FIG. 2 shows the PXRD pattern of Formula (I) as Form A. The peaks of the PXRD pattern is shown in Table 2, below. Any remaining Formula (I) as Form B can be removed by repeating the recrystallization.

TABLE 2

PXRD peaks of Form A of Formula (I)

| 2-Theta | d-spacing [Å] | Height | H % |
|---|---|---|---|
| 7.180 | 12.3018 | 1429 | 31 |
| 9.420 | 9.3810 | 1216 | 26 |
| 9.700 | 9.1108 | 325 | 7 |
| 9.900 | 8.9272 | 257 | 6 |
| 10.720 | 8.2461 | 335 | 8 |
| 11.120 | 7.9504 | 283 | 7 |
| 13.660 | 6.4772 | 180 | 4 |
| 14.300 | 6.1887 | 813 | 18 |
| 14.540 | 6.0871 | 1701 | 37 |
| 14.680 | 6.0294 | 808 | 18 |
| 16.540 | 5.3553 | 1091 | 24 |
| 16.900 | 5.2420 | 1218 | 26 |
| 17.120 | 5.1751 | 877 | 19 |
| 17.760 | 4.9901 | 569 | 13 |
| 18.260 | 4.8545 | 4690 | 100 |
| 18.820 | 4.7113 | 644 | 14 |
| 19.080 | 4.6477 | 3893 | 83 |
| 19.380 | 4.5764 | 201 | 5 |
| 19.840 | 4.4714 | 213 | 5 |
| 20.480 | 4.3331 | 352 | 8 |
| 20.960 | 4.2349 | 1818 | 39 |
| 21.700 | 4.0921 | 492 | 11 |
| 21.980 | 4.0406 | 1720 | 37 |
| 22.260 | 3.9904 | 587 | 13 |
| 22.540 | 3.9415 | 525 | 12 |
| 23.300 | 3.8146 | 247 | 6 |
| 23.580 | 3.7699 | 258 | 6 |
| 23.880 | 3.7233 | 257 | 6 |
| 24.460 | 3.6363 | 242 | 6 |
| 25.920 | 3.4347 | 330 | 8 |
| 25.960 | 3.4295 | 332 | 8 |
| 26.260 | 3.3910 | 598 | 13 |
| 27.060 | 3.2925 | 214 | 5 |
| 27.720 | 3.2156 | 440 | 10 |
| 28.000 | 3.1841 | 380 | 9 |
| 28.340 | 3.1466 | 342 | 8 |
| 28.420 | 3.1380 | 450 | 10 |
| 28.840 | 3.0932 | 300 | 7 |
| 29.040 | 3.0724 | 502 | 11 |
| 29.440 | 3.0315 | 632 | 14 |
| 27.720 | 3.0036 | 870 | 19 |
| 30.460 | 2.9323 | 292 | 7 |
| 30.640 | 2.9155 | 280 | 6 |
| 31.140 | 2.8698 | 237 | 6 |
| 31.260 | 2.8590 | 218 | 5 |
| 31.360 | 2.8502 | 236 | 6 |
| 32.100 | 2.7861 | 290 | 7 |
| 35.280 | 2.5419 | 306 | 7 |
| 35.720 | 2.5116 | 456 | 10 |
| 37.000 | 2.4276 | 251 | 6 |
| 37.120 | 2.4200 | 213 | 5 |
| 38.540 | 2.3341 | 378 | 9 |
| 39.320 | 2.2896 | 246 | 6 |

The PXRD patterns obtained in Example 1 were obtained with a Rigaku RINT TTR III diffractometer using Cu Kα (50 kV/300 mA) radiation.

Example 2: Solubility Study of Formula (I)

Solubility was assessed in an array of diverse solvents in order to facilitate the selection of solvent systems and corresponding dosing strategies for the subsequent crystal-form screening experiments. The solubility of Form A of Formula (I) was visually estimated in 12 solvents at RT, and if applicable, at 40° C. by dosing small aliquots of the solvent into a fixed amount of the API (10.0 mg) until the dissolution point or a maximum volume of 1.8 mL was reached. As shown in Table 3, Formula (I) exhibits moderate solubility (21-52 mg/mL) in DMSO, and low solubility (≤7 mg/mL) in all other solvents evaluated.

TABLE 3

Solubility Study Results

| Trial # | Solvent (v/v) | Solubility at RT (mg/mL) | Solubility at 40° C. (mg/mL) |
|---|---|---|---|
| 1 | DMSO | 21-52 | n/a |
| 2 | Toluene | <7 | <7 |
| 3 | MeOH | <7 | <7 |
| 4 | THF | <6 | <6 |
| 5 | MeCN | <6 | <6 |
| 6 | IPA:water (9:1) | <6 | <6 |
| 7 | DCM | <6 | <6 |
| 8 | MTBE | <6 | <6 |
| 9 | Water | <6 | <6 |
| 10 | IPA | <6 | <6 |
| 11 | EtOAc | <6 | <6 |
| 12 | IPE | <6 | <6 | n/a = not applicable

Example 3: Polymorph Screening Study of Formula (I)

Overview

The polymorph screening study of Formula (I) involved ~156 crystallization experiments which were complemented by focused experiments aiming at reproducing and/or characterizing novel/important crystal forms.

Solvent Selection

Sixty solvent systems were utilized as neat and binary mixtures to provide a diverse set of polarities, dielectric constants, dipole moments, and hydrogen-bond donor/acceptor attributes. Water containing solvents with a variety of water activities were also included, e.g., See G. M. Wilson, *J. Am. Chem. Soc.* 1964, 86(2) pp. 127-133 and Bell G. et al., *Enzyme Microb. Technol.*, 1997, 20(6), pp. 471-477.

Crystallization Modes

The polymorph screening study employed the following crystallization modes using Form A of Formula (I) (API) as the input material:

a) Thermocycling (TC): API was added to HPLC vials and solvent (1 mL) was added. Samples were stirred at RT for 1 hour and observations on dissolution were made. Samples were stirred at 50° C. for 1 hour and observations on dissolution were made again. Samples were TC'ed between 50-5° C. for 96 hours. Solids were collected and air-dried on a filter plate for 4 hours. (TC, n=48)

b) Recrystallization (RC): Sample vials from TC were stirred and heated to 50° C. A clarifying filtration was performed at 50° C. and the filtrate was added to a clean 2 mL vial. The vial was placed in a freezer at −20° C. for 3-4 days, then moved to a 5° C. refrigerator for 16-24 hours. Solids were collected as above. (RC, n=48)

c) Evaporation (EV): Solutions from RC experiments were slowly evaporated in a fume hood over 10 days. Experiments that gave solids from RC were re-filtered and filtrate was evaporated as above.

d) Anti-solvent addition (ASA): Anti-solvent was added to saturated and clarified solutions of API at RT (ASA, n=12)

Analysis of Screening Products

FT-Raman spectroscopy was chosen as the primary method for analysis and grouping of samples. Representative samples from the groupings were analyzed by PXRD to verify their uniqueness. Where possible/practical, a representative sample of the unique group was further characterized by PLM, DSC, and TGA-IR.

Results

As shown in Table 4 and Table 5, the polymorph screen of Formula (I) produced three crystal forms:

Form A—predominant output of screen

Form C—monohydrate form

Form D—non-solvated form observed in several EV experiments

Form B, the crystal formed during the initial precipitation of Formula (I) in Example I, was not observed during the screening described within Example 3. Form E, another monohydrate crystal form, was identified in a batch of non-recrystallized Formula (I) but was not observed during the screening described within Example 3. As shown in Tables 4 and 5, the parent free acid form of Formula (I) ("Parent") was also observed in several solution-phase experiments over the course of the screen.

TABLE 4

Products of Slurry, Cooling, and Evaporation Crystallizations

| Trial # | Solvent | TC | RC | EV | Water activity |
|---|---|---|---|---|---|
| 1 | Water | A | | | |
| 2 | MeOH | A | | A | |
| 3 | 2-Methoxyethanol | A | | | |
| 4 | 1-Propanol | A | | Parent | |
| 5 | Nitromethane:20% DMSO | A | | | |
| 6 | MeCN | A | | | |
| 7 | DMSO | A | | A | |
| 8 | Acetone | A | | | |
| 9 | 2-Butanone | A | | | |
| 10 | DCM | A | A | D | |
| 11 | Methyl acetate | A | | | |
| 12 | 4-Methyl-2-pentanone | A | | | |
| 13 | Chloroform | A | | D | |
| 14 | EtOAc | A | | | |
| 15 | Clorobenzene:20% DMSO | A | | Parent | |
| 16 | THF | A | | Unknown | |
| 17 | 1,4-Dioxane | A | | | |
| 18 | Isopropyl ether | A | | | |
| 19 | Toluene:20% DMSO | A | | Parent | |
| 20 | Cyclohexane | A | | | |
| 21 | Heptane | A | | | |
| 22 | 1-Butanol | A | | | |
| 23 | IPA | A | | | |
| 24 | Trifluoroethanol | | | D | |
| 25 | Dimethyl carbonate | A | | | |
| 26 | MTBE | A | | | |
| 27 | Isopropyl acetate | A | | | |
| 28 | Ethanol | A | | Parent | |
| 28 | 1-Methoxy-2-propanol | A | | | |
| 30 | Cyclohexanone | A | | | |
| 31 | DMF | A | | Parent | |
| 32 | 2-Methoxyethyl ether | A | | | |
| 33 | MeOH:water (95:5) | A | | | 0.20 |
| 34 | MeCN:water (95:5) | A | | Amorph. | 0.60 |
| 35 | Acetone:water (95:5) | A | | Parent | 0.63 |

TABLE 4-continued

Products of Slurry, Cooling, and Evaporation Crystallizations

| Trial # | Solvent | TC | RC | EV | Water activity |
|---|---|---|---|---|---|
| 36 | THF:water (95:5) | A, C | C | C, D | 0.88 |
| 37 | IPA:water (95:5) | A | | | 0.54 |
| 38 | MeOH:water (90:10) | A | | A | 0.33 |
| 39 | MeCN:water (90:10) | A | | A | 0.76 |
| 40 | Acetone:water (90:10) | A | | Parent | 0.77 |
| 41 | THF:water (90:10) | A, C | C | C, D | 0.94 |
| 42 | 1,4-Dioxane:water (90:10) | A | | C, D | 0.69 |
| 43 | 2-Propanol:water (90:10) | A | | A | 0.76 |
| 44 | Acetone:water (80:20) | A | | A | 0.86 |
| 45 | Ethanol:water (20:80) | A | | A | 0.95 |
| 46 | 2-Propanol:DMSO (80:20) | A | | | |
| 47 | MeCN:DMSO (80:20) | A | | Parent | |
| 48 | NMP | | | Parent | |

TABLE 5

Products of Anti-Solvent Addition

| Trial # | Solvent | Anti-Solvent | Result |
|---|---|---|---|
| 1 | NMP | Water | Parent |
| 2 | NMP | DCM | |
| 3 | NMP | 1,4-Dioxane | |
| 4 | DMF | EtOAc | A |
| 5 | DMF | Acetone | A |
| 6 | DMF | Water | Parent |
| 7 | Trifluoroethanol | THF | A |
| 8 | Trifluoroethanol | Water | Parent |
| 9 | Trifluoroethanol | Toluene | |
| 10 | DMSO | Water | Parent |
| 11 | DMSO | MeOH | A |
| 12 | DMSO | Heptane | |

TABLE 6

Legend for Table 4 and 5

| A | Form A | Non-solvated |
|---|---|---|
| B | Form B | Unknown |
| C | Form C | Hydrate |
| D | Form D | Non-solvated |
| E | Form E | Hydrate |
| Parent | Parent | Free acid |
| Unknown | Others | Melted under Raman laser |
| Amorph. | Amorphous | |
| [blank] | No solids formed | |

3.1 Descriptions of Polymorph Forms

3.1.1. Form A

Form A is a non-solvate form that was the predominate output of the polymorph screen. Form A of Formula (I), prepared as described above, was analyzed by FTIR, TGA, DSC, PXRD, and PLM (FIGS. 3A-3C). The PXRD pattern is shown in FIG. 3A. The peaks of the X-ray powder diffraction pattern is shown in Table 7, below. DSC shows a composite endotherm at a 239.9° C. occurring with decomposition and TGA-IR indicates 0.2% weight loss from 25-150° C. (FIG. 3B). The FTIR spectrum is shown in FIG. 3C. Form A is crystalline by PXRD and PLM analyses.

TABLE 7

PXRD peaks of Form A of Formula (I)

| 2-Theta | d-spacing [Å] | Height | H % |
|---|---|---|---|
| 7.354 | 12.0211 | 1299.28 | 14.29 |
| 9.6097 | 9.20384 | 2207.07 | 24.28 |
| 9.8795 | 8.95315 | 411.98 | 4.53 |
| 10.9013 | 8.1161 | 386.71 | 4.25 |
| 11.288 | 7.83895 | 397.87 | 4.38 |
| 13.8349 | 6.40106 | 352.18 | 3.87 |
| 14.4808 | 6.11696 | 1403.21 | 15.44 |
| 14.7266 | 6.01539 | 2536.5 | 27.9 |
| 16.72 | 5.30246 | 2690.2 | 29.59 |
| 17.0796 | 5.19162 | 2738.6 | 30.13 |
| 17.3204 | 5.12 | 1686.2 | 18.55 |
| 17.9363 | 4.94553 | 1459.49 | 16.06 |
| 18.4494 | 4.80914 | 8221.11 | 90.44 |
| 19.2796 | 4.60388 | 9090.24 | 100 |
| 20.6809 | 4.29499 | 860.4 | 9.47 |
| 21.1405 | 4.20264 | 2722.34 | 29.95 |
| 21.8788 | 4.06247 | 868.42 | 9.55 |
| 22.1825 | 4.00753 | 2831.8 | 31.15 |
| 22.4583 | 3.95894 | 901.03 | 9.91 |
| 22.741 | 3.91036 | 1093.49 | 12.03 |
| 24.0858 | 3.69499 | 422.2 | 4.64 |
| 24.6562 | 3.61078 | 391.08 | 4.3 |
| 26.119 | 3.41179 | 749.98 | 8.25 |
| 26.4676 | 3.36763 | 956.83 | 10.53 |
| 27.2553 | 3.27208 | 325.67 | 3.58 |
| 27.8546 | 3.20302 | 537.44 | 5.91 |
| 28.6329 | 3.1177 | 426.23 | 4.69 |
| 29.2535 | 3.05296 | 465.87 | 5.12 |
| 29.6127 | 3.01674 | 920.32 | 10.12 |
| 29.9169 | 2.98676 | 1012.9 | 11.14 |
| 30.7579 | 2.90698 | 233.71 | 2.57 |
| 31.4712 | 2.8427 | 146.69 | 1.61 |
| 32.277 | 2.77355 | 164.08 | 1.8 |
| 33.5909 | 2.66801 | 60.88 | 0.67 |
| 34.2015 | 2.62177 | 84.94 | 0.93 |
| 35.4955 | 2.5291 | 160.05 | 1.76 |
| 35.9176 | 2.50034 | 404.67 | 4.45 |
| 37.2266 | 2.41537 | 144.44 | 1.59 |
| 38.7491 | 2.3239 | 154.87 | 1.7 |
| 39.5228 | 2.28018 | 90.69 | 1 |

3.1.2 Form C

Form C is a monohydrate crystal form identified from the polymorph screen. It was observed as a mixture with Form A in two THF/water experiments in the TC mode. It was observed phase-pure in two RC experiments and as a mixture in two EV experiments. Form C of Formula (I), prepared as described above, was analyzed by FTIR, TGA, DSC, PXRD, and PLM (FIGS. 4A-4C). The PXRD pattern is shown in FIG. 4A. The peaks of the X-ray powder diffraction pattern is shown in Table 8, below. DSC shows a broad endotherm between 50-125° C. followed by two broad, shallow endotherms between 225-255° C. and TGA-IR indicates 3.2% stepwise weight loss of water between 25-175° C. (FIG. 4B). The FTIR spectrum is shown in FIG. 4C. Form C is crystalline by PXRD and PLM analyses.

TABLE 8

PXRD peaks of Form C of Formula (I)

| 2-Theta | d-spacing [Å] | Height | H % |
|---|---|---|---|
| 3.8583 | 22.90094 | 4098.76 | 40.1 |
| 7.6482 | 11.55936 | 1370.31 | 13.41 |
| 9.6007 | 9.21246 | 479.92 | 4.7 |
| 10.1069 | 8.75221 | 815.94 | 7.98 |
| 11.4738 | 7.71239 | 888.61 | 8.69 |
| 12.0116 | 7.36826 | 363.96 | 3.56 |

TABLE 8-continued

PXRD peaks of Form C of Formula (I)

| 2-Theta | d-spacing [Å] | Height | H % |
|---|---|---|---|
| 14.6915 | 6.02969 | 771.11 | 7.54 |
| 15.3189 | 5.78413 | 380.38 | 3.72 |
| 15.9486 | 5.55716 | 4171.23 | 40.81 |
| 16.7 | 5.30877 | 648.61 | 6.35 |
| 17.0004 | 5.21564 | 721.78 | 7.06 |
| 17.3039 | 5.12483 | 199.65 | 1.95 |
| 17.7942 | 4.98471 | 2543.19 | 24.88 |
| 18.4395 | 4.81169 | 1522.65 | 14.9 |
| 18.7001 | 4.74523 | 812.81 | 7.95 |
| 19.1844 | 4.62651 | 10220.65 | 100 |
| 19.5325 | 4.54485 | 1208.95 | 11.83 |
| 20.737 | 4.28349 | 967.87 | 9.47 |
| 21.1221 | 4.20626 | 351.77 | 3.44 |
| 21.472 | 4.13851 | 476.69 | 4.66 |
| 21.9503 | 4.04939 | 361.67 | 3.54 |
| 22.7193 | 3.91404 | 200.77 | 1.96 |
| 23.0684 | 3.8556 | 450.89 | 4.41 |
| 23.3093 | 3.81629 | 156.31 | 1.53 |
| 23.7996 | 3.73876 | 453.54 | 4.44 |
| 24.1525 | 3.68494 | 284.97 | 2.79 |
| 24.6784 | 3.60758 | 164.97 | 1.61 |
| 24.8974 | 3.57635 | 181.72 | 1.78 |
| 25.565 | 3.48446 | 328.95 | 3.22 |
| 25.8577 | 3.44567 | 428.99 | 4.2 |
| 26.7325 | 3.33487 | 1551.74 | 15.18 |
| 26.9871 | 3.30398 | 1331.62 | 13.03 |
| 28.3768 | 3.14526 | 2216.68 | 21.69 |
| 29.0984 | 3.06888 | 250.6 | 2.45 |
| 29.5911 | 3.0189 | 356.98 | 3.49 |
| 29.9472 | 2.9838 | 641.2 | 6.27 |
| 30.9228 | 2.89185 | 582.65 | 5.7 |
| 31.7397 | 2.81926 | 389.76 | 3.81 |
| 32.1961 | 2.78033 | 103.13 | 1.01 |
| 32.7288 | 2.73629 | 270.02 | 2.64 |
| 33.4078 | 2.68221 | 158.28 | 1.55 |
| 34.6917 | 2.58583 | 124.88 | 1.22 |
| 35.4385 | 2.53303 | 118.54 | 1.16 |
| 35.9922 | 2.49533 | 351.24 | 3.44 |
| 37.7608 | 2.38243 | 75.23 | 0.74 |
| 38.9205 | 2.31406 | 522.72 | 5.11 |
| 39.496 | 2.28166 | 328.76 | 3.22 |

3.1.3 Form D

Form D is a non-solvated form that was observed from several EV experiments. Form D of Formula (I), prepared as described above, was analyzed by FTIR, TGA-IR, DSC, PXRD, and PLM (FIGS. 5A-5C). The X-ray powder diffraction pattern is shown in FIG. 5A. The peaks of the PXRD pattern is shown in Table 9, below. DSC shows an endotherm at a 248.0° C. and TGA-IR indicates negligible weight loss (~0.6%) between 25-150° C. (FIG. 5B). The FTIR spectrum is shown in FIG. 5C. Form D is crystalline by PXRD and PLM analyses.

TABLE 9

PXRD peaks of Form D of Formula (I)

| 2-Theta (2Θ) | d-spacing [Å] | Height | H % |
|---|---|---|---|
| 7.0574 | 12.52561 | 18700.79 | 100 |
| 7.9356 | 11.14137 | 353.25 | 1.89 |
| 9.8816 | 8.95127 | 930.73 | 4.98 |
| 10.338 | 8.55709 | 376.86 | 2.02 |
| 11.2573 | 7.86023 | 2546.8 | 13.62 |
| 12.1499 | 7.28472 | 410.45 | 2.19 |
| 13.6201 | 6.50149 | 2154.9 | 11.52 |
| 13.8682 | 6.38575 | 3195 | 17.08 |
| 14.853 | 5.9645 | 1226.63 | 6.56 |
| 15.5157 | 5.7112 | 3451.54 | 18.46 |

TABLE 9-continued

PXRD peaks of Form D of Formula (I)

| 2-Theta (2Θ) | d-spacing [Å] | Height | H % |
|---|---|---|---|
| 16.1768 | 5.47928 | 2061.91 | 11.03 |
| 16.8476 | 5.2626 | 1721.83 | 9.21 |
| 17.1901 | 5.15851 | 4167.31 | 22.28 |
| 18.2452 | 4.86249 | 1569.98 | 8.4 |
| 18.5673 | 4.77887 | 2936.62 | 15.7 |
| 19.132 | 4.63906 | 1046.04 | 5.59 |
| 19.57 | 4.53621 | 8609.08 | 46.04 |
| 19.9171 | 4.45794 | 3724.72 | 19.92 |
| 20.3312 | 4.36807 | 1112.39 | 5.95 |
| 20.8234 | 4.26592 | 10676.47 | 57.09 |
| 22.5675 | 3.94003 | 777.89 | 4.16 |
| 23.2826 | 3.8206 | 608.46 | 3.25 |
| 23.8596 | 3.7295 | 863.21 | 4.62 |
| 24.1052 | 3.69206 | 877.77 | 4.69 |
| 24.3873 | 3.64998 | 2199.28 | 11.76 |
| 24.7158 | 3.60221 | 980.64 | 5.24 |
| 25.4155 | 3.50461 | 1294.59 | 6.92 |
| 25.9518 | 3.43339 | 1867.6 | 9.99 |
| 26.3058 | 3.38798 | 1473.92 | 7.88 |
| 27.8805 | 3.20011 | 3108.61 | 16.62 |
| 28.5697 | 3.12446 | 389.08 | 2.08 |
| 29.4261 | 3.03545 | 881.04 | 4.71 |
| 29.8937 | 2.98902 | 1151.2 | 6.16 |
| 31.0487 | 2.88041 | 1590.19 | 8.5 |
| 32.1271 | 2.78615 | 241.27 | 1.29 |
| 32.9846 | 2.71565 | 218.96 | 1.17 |
| 34.4232 | 2.60539 | 64.11 | 0.34 |
| 34.9833 | 2.56494 | 142.67 | 0.76 |
| 35.6296 | 2.51989 | 224.23 | 1.2 |
| 36.0671 | 2.49032 | 216.3 | 1.16 |
| 36.9047 | 2.4357 | 158.38 | 0.85 |
| 37.8634 | 2.3762 | 12.8 | 0.07 |
| 38.7097 | 2.32618 | 121.85 | 0.65 |
| 39.5632 | 2.27794 | 369.7 | 1.98 |

An overlay of the PXRD patterns of polymorph Form A, C, and D of Formula (I) is shown in FIG. 6.

3.1.4 Form E

Form E is a monohydrate form that was identified in a batch of non-recrystallized Formula (I). Form E of Formula (I) was analyzed by FTIR, TGA-IR, DSC, PXRD, and PLM (FIGS. 7A-7D). The X-ray powder diffraction pattern is shown in FIG. 7A. The peaks of the PXRD pattern is shown in Table 10, below. DSC shows a broad endotherm between 85-150° C., followed by an endotherm at 215.4° C. and TGA-IR analysis indicates step-wise weight loss of 3.1% water (1 eq.) occurring with the broad DSC endotherm (FIG. 7B). A second step-wise weight loss of 7.1% carbon dioxide (decomposition) is observed from 175-210° C. Form E and Form C are both monohydrate forms, but TGA-IR data suggests the water in Form E is more tightly bound (higher dehydration temperature) than Form C as shown in FIG. 7C. The FTIR spectrum is shown in FIG. 7D. Form E is crystalline by PXRD and PLM analyses.

TABLE 10

PXRD peaks of Form E of Formula (I)

| 2-Theta (2Θ) | d-spacing [Å] | Height | H % |
|---|---|---|---|
| 7.2966 | 12.11559 | 379.55 | 5.61 |
| 9.5623 | 9.24939 | 1830.85 | 27.04 |
| 9.8951 | 8.93903 | 3114.2 | 46 |
| 10.0716 | 8.7828 | 4930.77 | 72.83 |
| 11.6333 | 7.60703 | 520.37 | 7.69 |
| 12.1065 | 7.31073 | 1123.29 | 16.59 |
| 12.4849 | 7.09 | 3216.4 | 47.51 |

TABLE 10-continued

PXRD peaks of Form E of Formula (I)

| 2-Theta (2Θ) | d-spacing [Å] | Height | H % |
|---|---|---|---|
| 13.4432 | 6.58666 | 515.89 | 7.62 |
| 14.5869 | 6.07271 | 2000.94 | 29.55 |
| 14.8079 | 5.98258 | 3380.73 | 49.93 |
| 15.144 | 5.85053 | 1050.41 | 15.51 |
| 16.2705 | 5.44791 | 6770.65 | 100 |
| 16.5476 | 5.35731 | 4329.72 | 63.95 |
| 17.1537 | 5.16936 | 2435.07 | 35.97 |
| 18.685 | 4.74902 | 4919.66 | 72.66 |
| 19.1913 | 4.62487 | 3192.99 | 47.16 |
| 20.0443 | 4.42994 | 2162.51 | 31.94 |
| 20.6253 | 4.30644 | 2324.34 | 34.33 |
| 20.8644 | 4.25763 | 2189.16 | 32.33 |
| 21.1141 | 4.20785 | 2256.83 | 33.33 |
| 21.3456 | 4.16272 | 1843.54 | 27.23 |
| 21.5955 | 4.11511 | 892.6 | 13.18 |
| 21.9683 | 4.04611 | 4429.61 | 65.42 |
| 22.6578 | 3.92453 | 1186.88 | 17.53 |
| 23.0012 | 3.86671 | 576.57 | 8.52 |
| 23.4223 | 3.79813 | 2223.06 | 32.83 |
| 23.9918 | 3.70924 | 1185.23 | 17.51 |
| 24.3631 | 3.65356 | 1899.8 | 28.06 |
| 25.191 | 3.53532 | 416.2 | 6.15 |
| 25.7667 | 3.45764 | 557.11 | 8.23 |
| 26.2244 | 3.39832 | 2547.26 | 37.62 |
| 26.557 | 3.3565 | 756.92 | 11.18 |
| 26.807 | 3.32577 | 453.94 | 6.7 |
| 27.4016 | 3.25493 | 725.49 | 10.72 |
| 28.0113 | 3.18545 | 1371.01 | 20.25 |
| 28.402 | 3.14252 | 581.38 | 8.59 |
| 28.7821 | 3.10188 | 1209.41 | 17.86 |
| 29.423 | 3.03576 | 556.93 | 8.23 |
| 29.8568 | 2.99263 | 803.21 | 11.86 |
| 30.1577 | 2.96345 | 508.09 | 7.5 |
| 30.4206 | 2.93844 | 1357.81 | 20.05 |
| 30.668 | 2.91529 | 970.42 | 14.33 |
| 31.1723 | 2.86928 | 400.14 | 5.91 |
| 31.4979 | 2.84036 | 415.37 | 6.13 |
| 32.6157 | 2.74552 | 990.11 | 14.62 |
| 33.5301 | 2.67271 | 133.1 | 1.97 |
| 34.0515 | 2.63297 | 181.92 | 2.69 |
| 34.4303 | 2.60486 | 467.91 | 6.91 |
| 35.4786 | 2.53026 | 116.09 | 1.71 |
| 35.9278 | 2.49965 | 421.75 | 6.23 |
| 36.7644 | 2.44467 | 161.48 | 2.38 |
| 37.363 | 2.40687 | 296.13 | 4.37 |
| 38.8209 | 2.31977 | 55.33 | 0.82 |

The PXRD patterns obtained in Example 3 were obtained with a PANalytical X'Pert Pro diffractometer using Ni-filtered Cu Kα (45 kV/40 mA) radiation.

Example 4: Milling 21.98 kg of crystalline Form A Formula (I) was processed in a fluidized bed opposed jet mill (Model number 100AFG; Hosokawa Micron) at a feed rate of 8 kg/h under nitrogen at 0.6 MPa and 15,000 rpm. After milling, 20.9 kg (94.6% recovery) was collected and analyzed by laser diffraction dry particle size analyzer (HELOS&RODOS). The particle size distribution results are reported in Table 11.

TABLE 11

Particle Size Distribution Results

| Compound name | $D_{10}$ (μm) | $D_{30}$ (μm) | $D_{50}$ (μm) | $D_{70}$ (μm) | $D_{90}$ (μm) |
|---|---|---|---|---|---|
| Formula (I) | 0.63 | 1.36 | 2.29 | 3.57 | 5.8 |
| Specification | — | — | — | — | <15 |

Example 5: Relative Stability Studies

Relative stability studies were conducted at 25° C. to determine thermodynamic crystal stability at various water activity levels ranging from $a_w$=0 to $a_w$=0.94. Both non-solvated forms (Forms A and D) and hydrate forms (Form C and E) were ripened during the study.

Saturated suspensions of the Formula (I) were prepared by stirring excess API in the specified solvent system. The suspension was stirred overnight at 25° C. A clarifying filtration was performed and the filtrate was added to a 2 mL vial containing seeds or small quantities of the relevant forms. The resulting suspensions were stirred at 25° C. for seven days. The solids were isolated, air-dried for 45 minutes, and analyzed by FTIR.

The FTIR spectra are shown in FIG. 8A and FIG. 8B and indicate Form A was the only crystal form remaining after the ripening study. The results of the study are summarized in Table 12.

TABLE 12

Ripening Study Results

| Batch | Solvent (v/v) | Water Activity $(a_w)^3$ | Temp (° C.) | Ripened Forms* | Final Form (7 days) |
|---|---|---|---|---|---|
| A | DMSO | 0 | 25 | A, C, D | A |
| B | MeOH | 0 | 25 | A, C, D | A |
| C | 77% DMSO/water | 0.5 | 25 | A, C, D | A |
| D | 91% acetone/water | 0.76 | 25 | A, C, D | A |
| E | 83% water/DMSO | 0.94 | 25 | A, C, D | A |
| F | DMSO | 0 | 25 | A, E | A |
| G | MeOH | 0 | 25 | A, E | A |
| H | 77% DMSO/water | 0.5 | 25 | A, E | A |
| I | 91% acetone/water | 0.76 | 25 | A, E | A |
| J | 83% water/DMSO | 0.94 | 25 | A, E | A |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

The invention claimed is:

1. A crystalline compound of Formula (I):

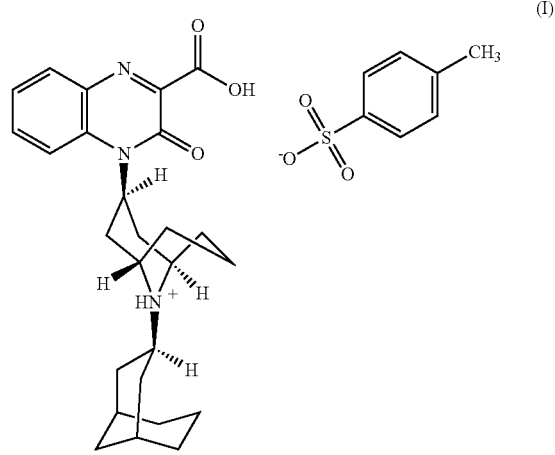

(I)

wherein the crystalline compound produces a powder X-ray diffraction spectrum comprising peaks at diffraction angles (2Θ±0.2°) of 18.5 and 19.3.

2. The crystalline compound of claim 1, wherein the powder X-ray diffraction spectrum further comprises peaks at diffraction angles (2Θ±0.2°) of 21.1 and 22.2.

3. The crystalline compound of claim 1, wherein the powder X-ray diffraction spectrum further comprises further comprising peaks at diffraction angles (2Θ±0.2°) of 7.4, 9.6, 14.7, and 16.7.

4. The crystalline compound of claim 1, wherein the powder X-ray diffraction spectrum further comprises peaks at diffraction angles (2Θ±0.2°) of 7.4, 9.6, 14.7, 16.7, 17.1, 21.1, and 22.2.

5. A crystalline compound of Formula (I):

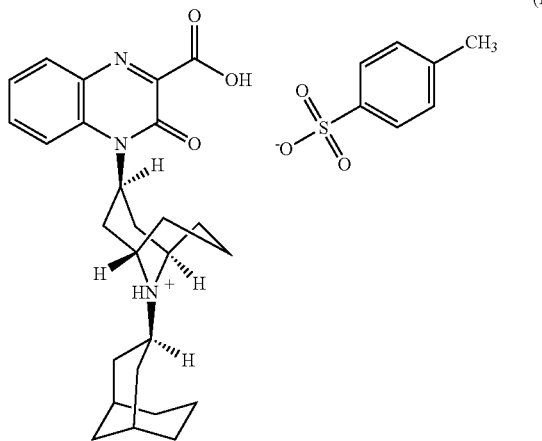

wherein the crystalline compound produces a powder X-ray diffraction spectrum comprising at least three peaks at diffraction angles (2Θ±0.2°) selected from the group consisting of 7.4, 9.6, 14.7, 16.7, 17.1, 18.5, 19.3, 21.1, and 22.2.

6. A crystalline compound of Formula (I):

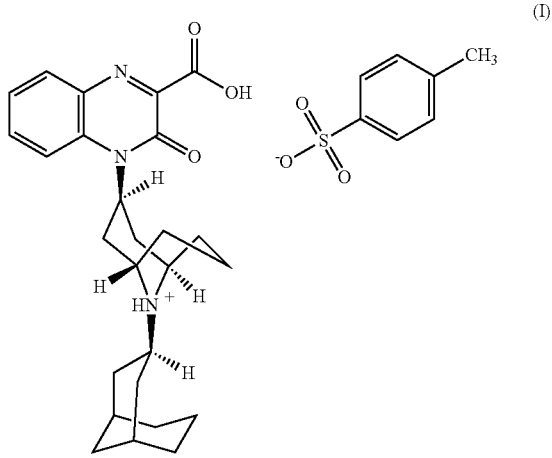

wherein at least about 90% by wt. of a total amount of the crystalline compound of Formula (I) is crystalline Form A, which produces a powder X-ray diffraction spectrum comprising at least three peaks at diffraction angles (2Θ±0.2°) selected from the group consisting of 7.4, 9.6, 14.7, 16.7, 17.1, 18.5, 19.3, 21.1, and 22.2.

7. The crystalline compound of claim 6, wherein at least about 95% by wt. of the crystalline compound of Formula (I) is crystalline Form A.

8. The crystalline compound of claim 6, wherein at least about 98% by wt. of the crystalline compound of Formula (I) is crystalline Form A.

9. The crystalline compound of claim 1, wherein the crystalline compound has a particle size $D_{90}$ of 15 μm.

10. The crystalline compound of claim 1, wherein the crystalline compound has a particle size $D_{90}$ of 8 μm.

11. The crystalline compound of claim 1, wherein the crystalline compound produces a powder X-ray diffraction spectrum as shown in FIG. 3A.

12. The crystalline compound of claim 1, wherein the crystalline compound has a differential scanning calorimetry (DSC) thermogram with an endothermic event having a peak temperature at about 241° C.

13. A pharmaceutical composition comprising the crystalline compound of claim 1 and at least one pharmaceutically acceptable excipient.

14. A dosage unit comprising from about 0.16 mg to about 8.0 mg of the crystalline compound of claim 1.

15. The dosage unit of claim 14, wherein the dosage unit is a solid oral dosage form.

16. The dosage unit of claim 15, wherein the solid oral dosage form is a tablet or capsule.

17. A process for producing the crystalline compound of claim 5 in crystalline Form A, comprising:

dissolving a compound of Formula (I) in formic acid to form a solution;

diluting the solution with ethyl acetate to form a diluted solution;

aging the diluted solution to form a slurry or seeding the diluted solution with a crystal of Form A to form a slurry; and filtering the slurry to isolate crystalline Form A.

18. The process of claim 17, further comprising the step of adding p-toluenesulfonic acid to the slurry.

19. A method for treating, preventing or managing a disorder comprising administering to an animal in need thereof an effective amount of the crystalline compound of claim 1, wherein the disorder is a sleep disorder.

20. The method of claim 19, wherein the sleep disorder is selected from the group consisting of insomnia; an alcohol-induced sleep disorder; insomnia in alcohol use disorder; a sleep disturbance associated with alcohol cessation; hypersomnia; circadian rhythm sleep-wake disorder; and any combination thereof.

* * * * *